(12) United States Patent
Leitermann et al.

(10) Patent No.: US 11,075,438 B2
(45) Date of Patent: Jul. 27, 2021

(54) RADIOFREQUENCY IDENTIFICATION EQUIPPED MEDICAL CABINET SYSTEMS AND METHODS OF ASSEMBLY AND USE THEREOF

(71) Applicant: WAVEMARK, INC., Concord, MA (US)

(72) Inventors: Richard Eugene Leitermann, Arlington, MA (US); Graham Davies, Chestnut Hill, MA (US); Leo Kiefer, Westford, MA (US); Lars Rohrberg, Groton, MA (US)

(73) Assignee: WAVEMARK, INC., Concord, MA (US)

( * ) Notice: Subject to any disclaimer, the term of this patent is extended or adjusted under 35 U.S.C. 154(b) by 0 days.

(21) Appl. No.: 16/688,953

(22) Filed: Nov. 19, 2019

(65) Prior Publication Data

US 2020/0161742 A1 May 21, 2020

Related U.S. Application Data

(60) Provisional application No. 62/770,020, filed on Nov. 20, 2018.

(51) Int. Cl.
*H01Q 1/22* (2006.01)
*G06K 7/10* (2006.01)
*G06Q 10/08* (2012.01)
*G16H 40/20* (2018.01)

(52) U.S. Cl.
CPC ....... *H01Q 1/2216* (2013.01); *G06K 7/10415* (2013.01); *G06Q 10/087* (2013.01); *G16H 40/20* (2018.01)

(58) Field of Classification Search
CPC .......... G06K 7/10356; G06K 7/10415; G06Q 10/087; G16H 40/20; H01Q 1/2216
See application file for complete search history.

(56) References Cited

U.S. PATENT DOCUMENTS

2004/0164864 A1* 8/2004 Chung ................... G07C 13/00
340/572.7
2006/0022827 A1* 2/2006 Higham .................. G07F 9/026
340/572.1

(Continued)

*Primary Examiner* — Sisay Yacob
(74) *Attorney, Agent, or Firm* — Arent Fox LLP

(57) ABSTRACT

An RFID-enabled storage container and systems and methods for assembly and use thereof. The RFID-enabled storage container may include adjustable shelving with built-in antennas, such that the shelving may be customized as may be needed. The system may include a storage container, an inventory management system, and one or more point of use terminals. The storage container may identify and check inventory stored thereon, and provide such information to the inventory management system. The storage container may notify the inventory management system when a product is no longer detected within its inventory, and the inventory management system may monitor the one or more point of use terminals to determine if the undetected product has been used at one of the point of use terminals. The inventory management system may also predict inventory needs as well as maintain age and other data for inventory and provide feedback via an illumination indication.

20 Claims, 19 Drawing Sheets

(56) References Cited

U.S. PATENT DOCUMENTS

| | | | |
|---|---|---|---|
| 2006/0238307 A1* | 10/2006 | Bauer | G08B 13/2474 |
| | | | 340/10.1 |
| 2009/0115579 A1* | 5/2009 | Chen | H04Q 9/00 |
| | | | 340/10.1 |
| 2015/0041537 A1* | 2/2015 | Gentile | G06K 7/08 |
| | | | 235/385 |
| 2015/0122887 A1* | 5/2015 | Morris | G06K 7/10356 |
| | | | 235/440 |
| 2016/0055447 A1* | 2/2016 | Sehmer | G06K 7/10415 |
| | | | 235/385 |
| 2017/0262797 A1* | 9/2017 | Wicks | H04W 4/80 |
| 2019/0073576 A1* | 3/2019 | D'Annunzio | G06K 19/0717 |

* cited by examiner

RADIOFREQUENCY IDENTIFICATION EQUIPPED MEDICAL CABINET SYSTEMS AND METHODS OF ASSEMBLY AND USE THEREOF

CROSS-REFERENCE TO RELATED APPLICATIONS

This Application claims priority to U.S. Provisional Application Number 62/770,020 filed Nov. 20, 2018, the contents of which are hereby incorporated by reference herein in their entirety.

TECHNICAL FIELD

Aspects of the present disclosure are directed to radiofrequency identification (RFID) enabled storage containers and systems and methods for assembly and use thereof.

SUMMARY

This background and summary are provided to introduce a selection of concepts in a simplified form that are further described below in the Detailed Description. This background and summary are not intended to identify key features of the claimed subject matter, nor are they intended to be used as an aid in determining the scope of the claimed subject matter.

RFID tags take the form of integrated circuits, with associated antennas, that have computer readable memory encoded with unique serial numbers (USNs), also referred to as unique identification numbers (UIDs). RFID tags typically can be encoded with other information in addition to unique serial numbers, either at the time of manufacture or thereafter, by writing data to a writeable or re-writable computer readable memory of the RFID tag. RFID tags are frequently used to identify and track objects. For example, RFID tags may be attached to any suitable object that may be tracked. RFID tags may uniquely identify their host object by associating the tag's UID with the object in a database or by writing information that identifies the object to the memory of the RFID tag. Such information may include an electronic product code (EPC), product serial number, manufacturing location, and/or any other information or code associated with the object.

An RFID tag reader may include or be coupled to an antenna used to generate a carrier signal that energizes the RFID tag antenna when the RFID tag is energized by the electromagnetic field generated by the reader's antenna. The energized RFID tag may generate a data signal that is transmitted by the tag's antenna and received by the RFID reader's antenna. The reader and/or its associated antenna may be in a fixed location or may be mobile, such as carried by an operator. For example, RFID readers are often placed at multiple, distributed locations associated within a supply chain in order to monitor the items having RFID devices placed thereon as they pass through manufacturing, transportation, distribution, storage, to consumption. Each reader may capture the UID of the RFID tag associated with each item as the RFID tag enters the reader's interrogation field, and data collected from all readers facilitates item tracking over time, through and within the supply chain.

Medical item cabinets may be equipped with one or more RFID readers to interrogate and read the contents of the RFID tags associated with the items stored in or near the cabinet to monitor or track the tagged items. Such cabinets typically include a computer (i.e., central processing unit (CPU)) that processes and/or stores information read from the RFID tags and serves as the communication hub for the cabinet. These cabinets are typically coupled via a primary communication channel to the Internet or other communications network (e.g., servers in a "cloud") using a wired or wireless (e.g., Wi-Fi) network adapter coupled to the cabinet's computer. This primary communication channel may be used to communicate information among the cabinet and remotely located servers or other computer systems, such as an inventory management system, for several purposes, including to: (i) send information read from medical item tags (i.e., bar code or RFID tags) from the cabinet to the cloud during or after a cabinet inventory read cycle; (ii) modify cabinet settings, such as the frequency of inventory read cycles; (iii) update software or firmware on the cabinet remotely; and/or (iv) send diagnostic commands to assess problems and obtain diagnostic information and logs.

RFID-enabled storage cabinets may allow real-time tracking of inventory. Using information obtained from RFID-enabled storage cabinets, inventory managers may be able to determine and/or infer what product inventory they have at a given location without manually tracking product inventory. Although conventional RFID-enabled storage cabinets may be customized such that they may be configured to accommodate boxed products, hanging products, doors, drawers, splitter shelves, etc., these RFID-enabled storage cabinets of the related art often may not be readily modified after manufacturing. That is, storage components of conventional RFID-enabled storage cabinets may be fixed in part due to the mechanical antenna elements used to traverse the storage components to scan for stored products.

Aspects of the present disclosure relate to an RFID-enabled storage container and systems and methods for assembly and use thereof In some implementations, an RFID-enabled storage container in accordance with aspects of the present disclosure may include adjustable shelving with built-in antennas, such that the shelving may be repositioned within the container as may be needed after the RFID-enabled storage container is manufactured. In some implementations, aspects of this customization may be achieved using storage components, e.g., shelving, dividers, or drawers having built-in antennas.

The systems and methods may include one or more devices, such as one or more computers or other terminal devices and/or computer systems, for managing inventory using the RFID-enabled storage container, among other functions. The system may include features for: (i) receiving ultrahigh frequency (UHF) and/or high frequency (HF) RFID signals and/or low frequency (LF) RFID signals including information associated with a plurality of products stored in the RFID-enabled storage container, (ii) associating additional information relating thereto, such as container identification and/or location information, and/or product location, quantity, and/or condition information, (iii) verifying or otherwise analyzing information received based on the RFID type (UHF, HF and LF), and/or (iv) monitoring the state of the products until final disposition.

Additional advantages and novel features of the systems and methods of the present disclosure will be set forth in part in the description that follows, and in part will become more apparent to those skilled in the art upon examination of the following or upon learning by practice of the disclosure.

BRIEF DESCRIPTION OF THE DRAWINGS

In the descriptions that follow, like parts are marked throughout the specification and drawings with the same numerals, respectively. The drawings are not necessarily drawn to scale and certain drawings may be shown in exaggerated or generalized form in the interest of clarity and conciseness. The disclosure itself, however, as well as a preferred mode of use, further features and advances thereof, will be understood by reference to the following detailed description of illustrative implementations of the disclosure when read in conjunction with reference to the accompanying drawings, wherein.

DETAILED DESCRIPTION

Figure 1:
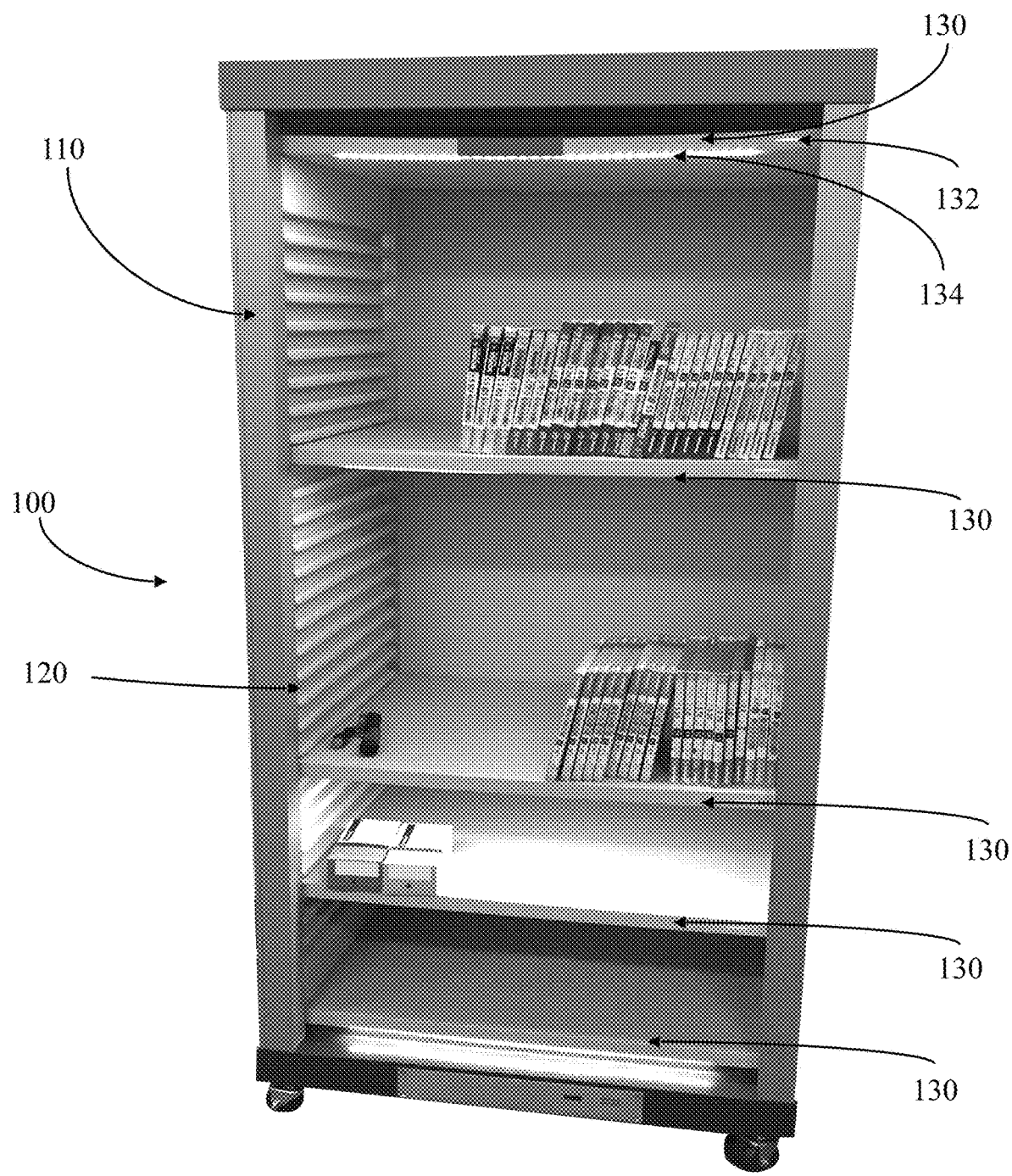
FIGS. 1, 2A, 2B and 3 illustrate views of various features implemented with an example storage container in accordance with aspects of the present disclosure.

The following includes definitions of selected terms employed herein. The definitions include various examples and/or forms of components that fall within the scope of a term and that may be used for implementation. The examples are not intended to be limiting.

A "processor," as used herein, processes signals and performs general computing and arithmetic functions. Signals processed by the processor may include digital signals, data signals, computer instructions, processor instructions, messages, a bit, a bit stream, or other computing that may be received, transmitted and/or detected.

A "bus," as used herein, refers to an interconnected architecture that is operably connected to transfer data between computer components within a singular or multiple systems. The bus may be a memory bus, a memory controller, a peripheral bus, an external bus, a crossbar switch, and/or a local bus, among others. The bus may also be a vehicle bus that interconnects components inside a vehicle using protocols, such as Controller Area network (CAN), Local Interconnect Network (LIN), among others.

A "memory," as used herein may include volatile memory and/or non-volatile memory. Non-volatile memory may include, for example, ROM (read only memory), PROM (programmable read only memory), EPROM (erasable PROM) and EEPROM (electrically erasable PROM). Volatile memory may include, for example, RAM (random access memory), synchronous RAM (SRAM), dynamic RAM (DRAM), synchronous DRAM (SDRAM), double data rate SDRAM (DDR SDRAM), and/or direct RAM bus RAM (DRRAM).

An "operable connection," as used herein may include a connection by which entities are "operably connected," is one in which signals, physical communications, and/or logical communications may be sent and/or received. An operable connection may include a physical interface, a data interface and/or an electrical interface.

A "wired or wireless connectivity," as used herein may include a universal serial bus (USB) connection, Wi-Fi connection, Bluetooth or Bluetooth Low Energy (BLE) connection, Ethernet connection, cable connection, digital subscriber line (DSL) connection, cellular connection (e.g., 3G, LTE/4G or 5G), or other suitable connections. The wired or wireless connectivity may communicative with a local area network (LAN), a wide area network (WAN), a cellular network, a WiFi network, a satellite network, an intranet, a metropolitan area network (MAN), the global Internet, a wired network, a wireless network, or any combination thereof.

As generally described herein, aspects of the present disclosure may provide for an RFID-enabled storage container and systems and methods for assembly and use thereof. For instance, an example system in accordance with aspects of the present disclosure may provide for tracking and/or monitoring of products through the supply chain and lifecycle of a product. This tracking/monitoring may be achieved using an RFID tag that enables various features and/or systems in accordance with aspects of the present disclosure to track the location of and/or monitor the status of one or more products at various locations and times throughout the supply chain, storage, and/or use of the products. Information collected with the assistance of the RFID tag may be used to provide analytics and insights into the supply chain, inventory management, and use of tagged products, among other uses. Additionally, the example system may track a variety of products from various origins and points of entry into the system, for example, wherein the products may have a variety of RFID tag types affixed thereto. Thus, the system may track products having LF RFID tags, HF RFID tags, or UHF RFID tags (and/or other tags, such as bar codes or other optical tags). Furthermore, various aspects of example systems may dynamically and automatically adapt to various product types, tags, and reader environments, among other features, in order to facilitate inventory tracking and reporting. Such techniques and/or other examples of techniques for managing inventory through the supply chain and lifecycle of a product are described, for example, in further detail in U.S. patent application Ser. No. 16/543,246, filed on Aug. 16, 2019, to Leitermann et al., the contents of which are herein incorporated by reference in their entirety.

One example storage container 100 and various features usable or implemented therewith, in accordance with aspects of the present disclosure, are illustrated in FIGS. 1, 2A, 2B and 3. In this example, storage container 100 may comprise a cabinet configured to store items associated with RFID tags, to read information from the RFID tags of stored items, and to communicate information associated with the tags, the products, and/or the storage container 100 to an inventory management system. In some implementations, the storage container 100 may be mobile, such that it may be relocated, rather than being permanently affixed to a single location after installation. In other implementations, the storage container may comprise an Office of Statewide Health Planning and Development (OSHPD) seismic mount for specific state building codes to protect the container from falling over during an earthquake. The storage container 100 may include a housing 110 having a plurality of slots 120 configured to support and/or provide communications with a respective shelf 130 located there within. In this way, the number of shelves 130 and spacing between each pair of adjacent shelves 130 implemented in the storage container 100 may be customized based on user needs and/or a size of an object stored thereon, for example.

Figure 2A:
Figure 2B:
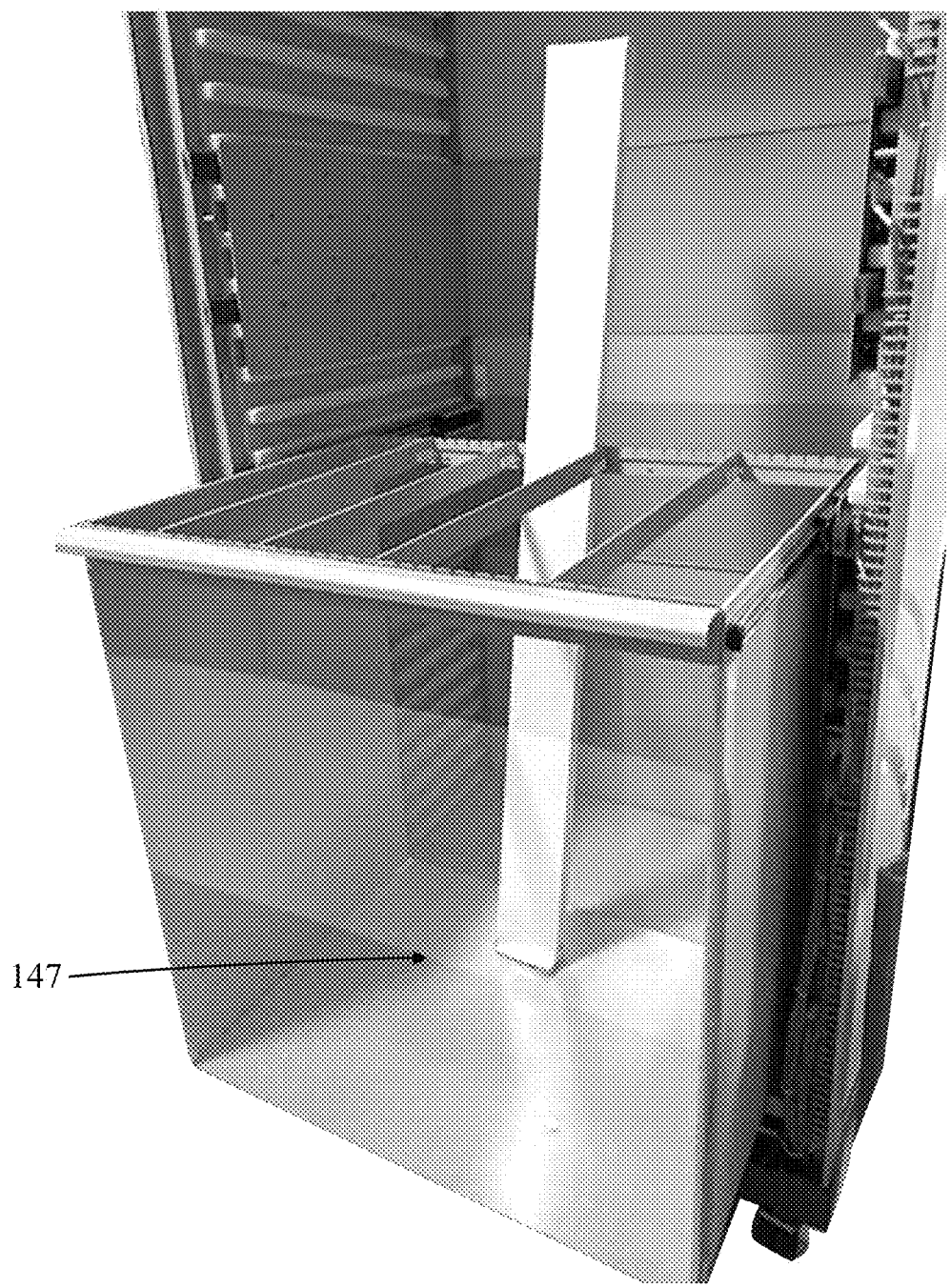

In some implementations, the storage container may include one or more hanging features 145 for hanging one or more products, as illustrated in FIG. 2A. For example, an RFID tag may be applied to one or more products stored in the storage container 100. The RFID tags may be formed in a variety of designs, for example, the RFID tag may be designed to be directly attached onto a surface of a product by lying flat, or the RFID tag may be designed to partially attach to a product by partly overhanging on an edge in order to be used in conjunction with the hanging features 145 (see, e.g., U.S. patent application Ser. No. 12/258,847, filed on Oct. 27, 2008, now issued U.S. Pat. No. 8,174,392, the contents of both of which are hereby incorporated in their entirety herein by reference). In some implantations, the storage container may also include one or more accessory standing bin(s) 147 for containing/holding one or more taller products that may not be readily accommodated by the hanging features 145 or the shelves 130, as illustrated in FIG. 2B. In one aspect, the accessory standing bin 147 may be removable, for example via wheels, from the overall storage container 100. The removability of the standing bin 147 may provide users access to the larger products that are contained in the standing bin 147, for example, allowing users to place and/or remove the larger products from the standing bin 147 contained within the storage container 100.

Figure 3:

In some implementations, as illustrated in FIG. 3, a bottom shelf 130a, for example, may be designed to at least partially conceal additional hardware components and/or software features that interact with other, corresponding features of the storage container.

For example, as illustrated in FIG. 1, some of the shelf features may optionally include a status light 132 to indicate the status of products stored and/or identified on that or a nearby shelf 130. In some instances, the status light 132 may be placed on a front face of the shelf 130, such that the status light is readily visible to an observer of the storage container 100. The status light 132 may indicate whether there are missing products, expired products, and/or products near expiration, for example. Alternatively, the status light 132 may indicate that there are no such issues with any of the products stored and identified on a shelf 130. In another aspect of the disclosure, the status light may provide an indication of the operating status of a specific shelf 130 and/or container. For example, the status light 132 may flash, thereby indicating that the shelf is being activated (e.g., is powered or otherwise operable), and/or has been placed in an active state. In another example, the status light 132 may provide an indication that the container is rebooting and/or in a start-up or shut-down state. In another example, the status light 132, may indicate an error with the shelf or shelves; for example, the status light 132 may indicate that a shelf is not properly connected to the storage container 100, or is not in communication with the storage container 100. The status light 132 may be implemented in a variety of colors, intensities, sequences, etc. The status light 132 may comprise light emitting diodes (LEDs), organic light emitting diodes (OLEDs), or other suitable types of illumination devices.

Additionally, as further illustrated in FIG. 1, in some implementations, each shelf 130 may also include one or more tracking light(s) 134, which may be used, for example, to illuminate nearby products or to indicate the location(s) of one or more products within the storage container 100. In an aspect of the disclosure, the tracking lights 134 may be affixed to the front of the specific shelf or may be affixed to the bottom of the specific shelf. For example, an illuminated tracking light 134 may be affixed to a front of a shelf 130 and may be implemented to visually indicate information about a product or a corresponding location of a specific product using an illuminated tracking light 134. For example, the tracking light 134 may be affixed to the front of the shelf to provide a visual indication of the status (e.g., expiration status) of one or more products to a user. Further, in another example, an illuminated tracking light 134 may be affixed to a bottom of a shelf and may be used to visually indicate and illuminate a location (e.g., the positon of a product located on a shelf below a portion of the illuminated tracking light). For example, the tracking light 134 may be affixed to the bottom of the shelf thereby indirectly illumining an area to identify a product location and/or status of a product to a user.

In one aspect of the disclosure, the illuminated tracking light 134 may be controlled by the controller 180 and/or the control unit 140, as described further below with reference to FIGS. 7-12, and may be controlled in conjunction with operation of an inventory management system 1120, as described further below with reference to FIG. 13. For example, the tracking light 134 may be activated to provide and illuminate at different levels of intensity, different colors, different portions, different times and/or a combination thereof. In one aspect of the disclosure, the tracking light 134 may provide visual indications to a user for location identification purposes. For example, based upon the location of a product (e.g., as identified by various features of the storage container), the tracking light 134 may be controlled by the controller 180 and/or the system (e.g., inventory management system 1120 of FIG. 13) to provide indication of the location of the product. For example, a user may wish to find product A within storage container 1. Product A may be located, based on a previous or current read of the storage container 1, at or near the front left side of shelf 1. The tracking light 134 may then be controlled to illuminate in a white color at a brightness of 50%, for example, on the left side portion of shelf 1 so as to indicate to the user the location of the requested product A. In one aspect of the disclosure, a user may request a specific product location to be indicated by activating the tracking light 134, or the tracking light 134 may be automatically activated based upon specific programming events. For example, product B may be located, based on a previous or current read of the storage container 100, at or near the front right side of shelf 2. The system (e.g., system 1100 of FIG. 13) may determine that product B may be near its expiration date, and as a result of this determination, the system may trigger activation of tracking light 134. The tracking light 134 may be controlled to illuminate at a brightness of 100% for 1 second and a brightness of 0% for 1 second (i.e., flashing), for example, in a yellow color on the right side portion of shelf 2. Such operation may readily indicate to the user that the product is located in the position highlighted and that the product is about to expire.

In another aspect of the disclosure, the tracking light 134 may provide visual indications to a user for other inventory purposes. For example, the tracking light 134 may be automatically activated based upon specific programming events regarding inventory within the storage container 100. In this example, the tracking light 134 may automatically be activated based upon the quantity of specific products read by the storage container 100, as compared to a threshold or a plurality of thresholds. Thus, for example, if the quantity of a specific product drops below a first threshold, the tracking light 134 may automatically be activated to indicate that the product quantity is less than the desired amount to be stored within the storage container 100. In another example, if the quantity of a specific product drops below a minimal storage amount threshold, the tracking light 134 may automatically activate to indicate to a user that a product quantity is at a critically low level. For example, if any specific product quantity within the storage container is 5 or less, the tracking light 134 may be activated to indicate that the product is running low (for example, a portion of the tracking light on a specific shelf for which the product is located illuminates to yellow). In another example, if any specific product quantity within the storage container is 2 or less, the tracking light 134 may be activated indicating the product is nearing complete exhaustion (for example, a portion of the tracking light on a specific shelf for which the product was previously located illumined to red).

In yet another aspect of the present disclosure, a user may request a specific visual inventory count to be indicated by activating the tracking light 134 on demand. For example, products of variety B (for example, catheters) may be located, based on a previous or current read of the storage container 100, at or near the front right side of shelf 2. The system (e.g., system 1100 of FIG. 13) may determine that products of the variety of B are low in comparison to a threshold, and therefore may trigger the activation of low supply tracking light 134. The low supply tracking light 134 may be controlled to illuminate at a brightness of 100%, in a yellow color on the right side portion of shelf 2, so as to indicate that products of a variety of B are running low in comparison to the threshold.

The tracking light 134 may be implemented in a variety of colors, intensities, sequences, etc. The tracking light 134 may comprise LEDs, OLEDs, or other suitable types of illumination devices. Further, as described above, the tracking light 134 may be set with specific illumination programming patterns and/or sequences generated during construction of the device and/or updated dynamically based upon a request by a user. For example, the tracking light 134 in conjunction with the controller 180, the control unit 140 and/or the inventory management system 1120 may be pre-programed with default specific threshold levels, indication sequences, etc. (for example, illumining yellow when the product quantity is low). In another example, a user of the storage container 100 may change the pre-programed defaults on site dynamically (for example, adjusting the tracking light 134 to flash faster when illuminating, changing colors in a different pattern based upon an expired product, etc.).

Figure 4:
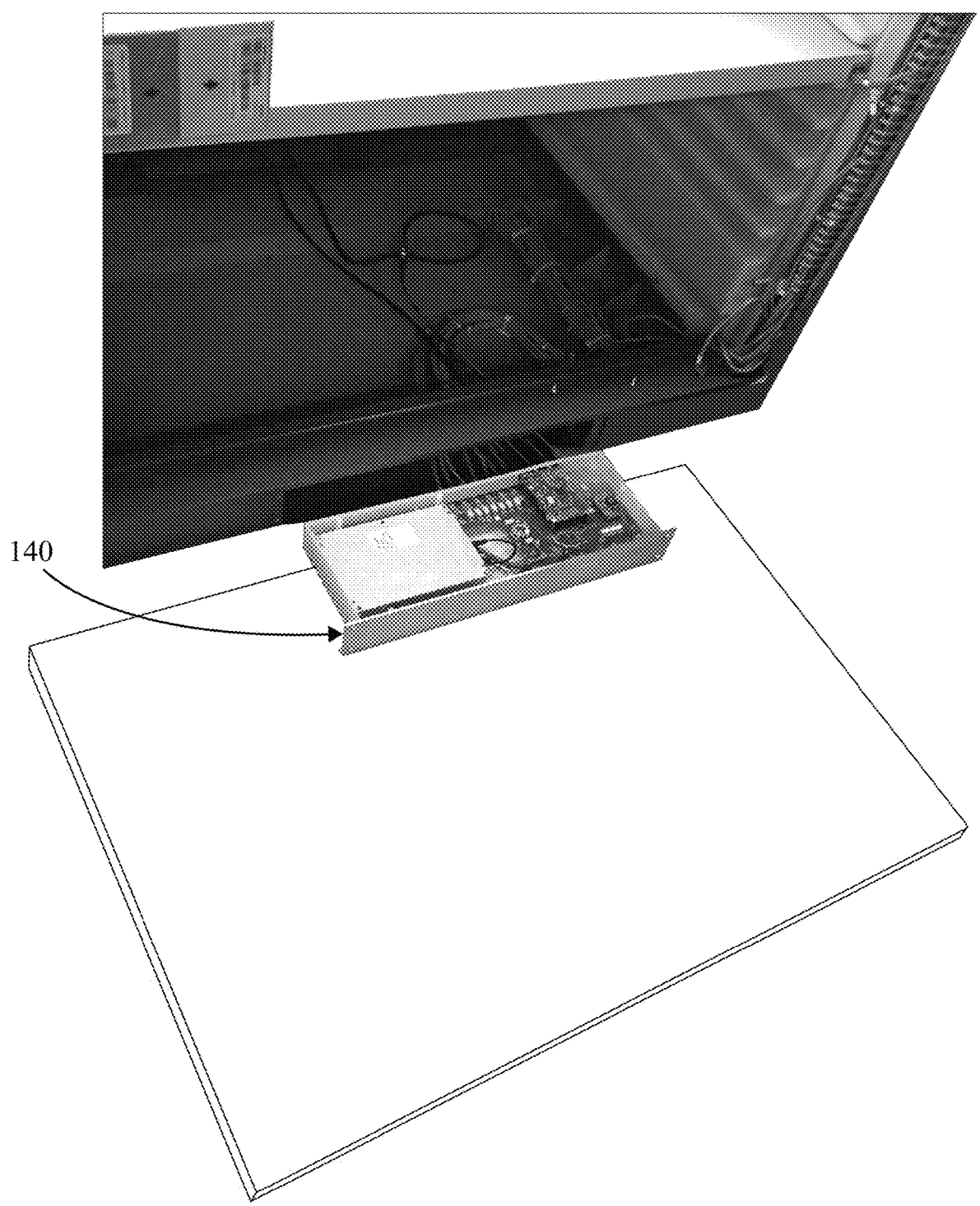
FIGS. 4-5 illustrate an example control unit for use in accordance with aspects of the present disclosure.
Figure 5:

In some aspects, as illustrated in FIGS. 4 and 5, the storage container 100 may include a control unit 140 that may be communicatively coupled to the shelves 130 housed within the plurality of slots 120. In some implementations, the bottom shelf 130a (FIG. 3), for example, may also be used to cover and/or partially contain one or more features of the control unit 140. The control unit 140 may include an internal power supply 146, such as a battery, and/or may be coupled to an external power supply. In one aspect of the disclosure, if a storage container 100 is disconnected from the power supply (for example, the power supply 146 is actively disconnected, a loss of power from the grid occurs, and/or a system failure occurs), an automatic "last gasp" error message may be transmitted, such as via wired or wireless communication with a nearby storage container. For example, when a storage container 100 is unplugged, turned off, or disconnected from the primary wired network port, a determination may be made only that the storage container 100 is no longer coupled to or communicating with other components, and it may not be possible to determine why or what went wrong so as to cause such failure. However, a battery backup may be capable of running the storage container 100 for a period of time after the storage container 100 has been disconnected from the power supply. The "last gasp" message may thus be sent to a nearby storage container 100'. The "last gasp" message may contain data, for example, indicating that a user has purposively turned off the storage container 100, a user has purposively unplugged the storage container 100 from the power supply, or the storage container 100 has some other failure such that the container 100 is no longer able to be communicated with. A notification may then be generated so as to allow the failure to be corrected and/or otherwise addressed.

In another aspect of the disclosure, the storage container 100 may comprise wired or wireless connectivity to aid in the processes of running diagnostics, initially setting-up the network settings of each storage container, providing upgrades to software (for example, update and/or replace the operating software), and/or retrieving and enabling review of storage container logs. For example, the storage container 100 (FIG. 1) may be capable of directly communicating wirelessly, via Bluetooth®, with mobile device 1150 illustrated in FIG. 13. The mobile device 1150 may comprise a proprietary application (App), that may provide a user with access to settings of the specific storage container 100 during a configuration process, set-up process, re-configuration process, etc.

Referring to FIG. 5, the control unit 140 may also include an RFID reader 142 for generating carrier signals to energize the RFID tags and for reading the data signal transmitted or reflected by each tag's antenna in response to being energized. This energizing and reading process may be referred to as "conducting a scan." In one aspect of the disclosure, the storage container 100 (FIG. 1) in conjunction with operation of the inventory management system 1120 of FIG. 13, may provide, for example, for detection and correction of operational "flicker." Such flicker may be characterized as occurring when RFID tags are not consistently read by a storage container 100 because the RFID tags may be on the threshold of readability, for example. Thus, some RFID tags may be read by the RFID reader 142 during one or more scans, but the same tag may not be read by the RFID reader 142 during one or more other scans. A determination may then be made that a flicker of a tag or tags has occurred. In one aspect of the disclosure, the storage container in conjunction with processing via the inventory management system 1120 of FIG. 13, for example, may determine that a varying number of RFID tags are read between subsequent scans at the same operating power levels, and thus a flicker may have occurred. For example, a first scan may occur at 12:01 AM at 1 watt, when 50 discrete RFID tags may be read. A second scan may occur at 12:04 AM at 1 watt, when 48 discrete RFID tags may be read. A third scan may occur at 12:07 AM at 1 watt, when 49 discrete RFID tags may read. A determination may then be made that a flicker has occurred based upon the quantity of the RFID tags read changing repeatedly with the scans conducted.

In another aspect of the disclosure, the storage container in conjunction with the inventory management system 1120 of FIG. 13, described below, a determination may be made that a varying number of RFID tags are read between subsequent scans at differing operating power levels, and thus a flicker may have occurred.

In one aspect of the disclosure, a determination may be made by a storage container 100 that a flicker may have occurred, and an attempt may be made to correct the flicker by adjusting the storage cabinet to a higher operating power level for one or more subsequent scans. In one aspect of the disclosure, a higher operating power level of scans may allow for proper reading of all tags contained within the storage container 100. For example, the storage container 100 may initially operate at an operating power level of ¼ watt, and based on the determined flicker, the storage container may increase the operating power level to 1 watt for one or more subsequent scans. As an example alternative to varying the power level, the storage container 100 may also vary the RFID read strategy. Varying read strategies, and other similar techniques for identifying and addressing flicker, along with filtering cross-reads of RFID tags are described, for example, in further detail in U.S. Patent Application No. 62/936,114, filed on Nov. 15, 2019, to Richard Leitermann et al., which is incorporated by reference herein in its entirety.

Figure 6:
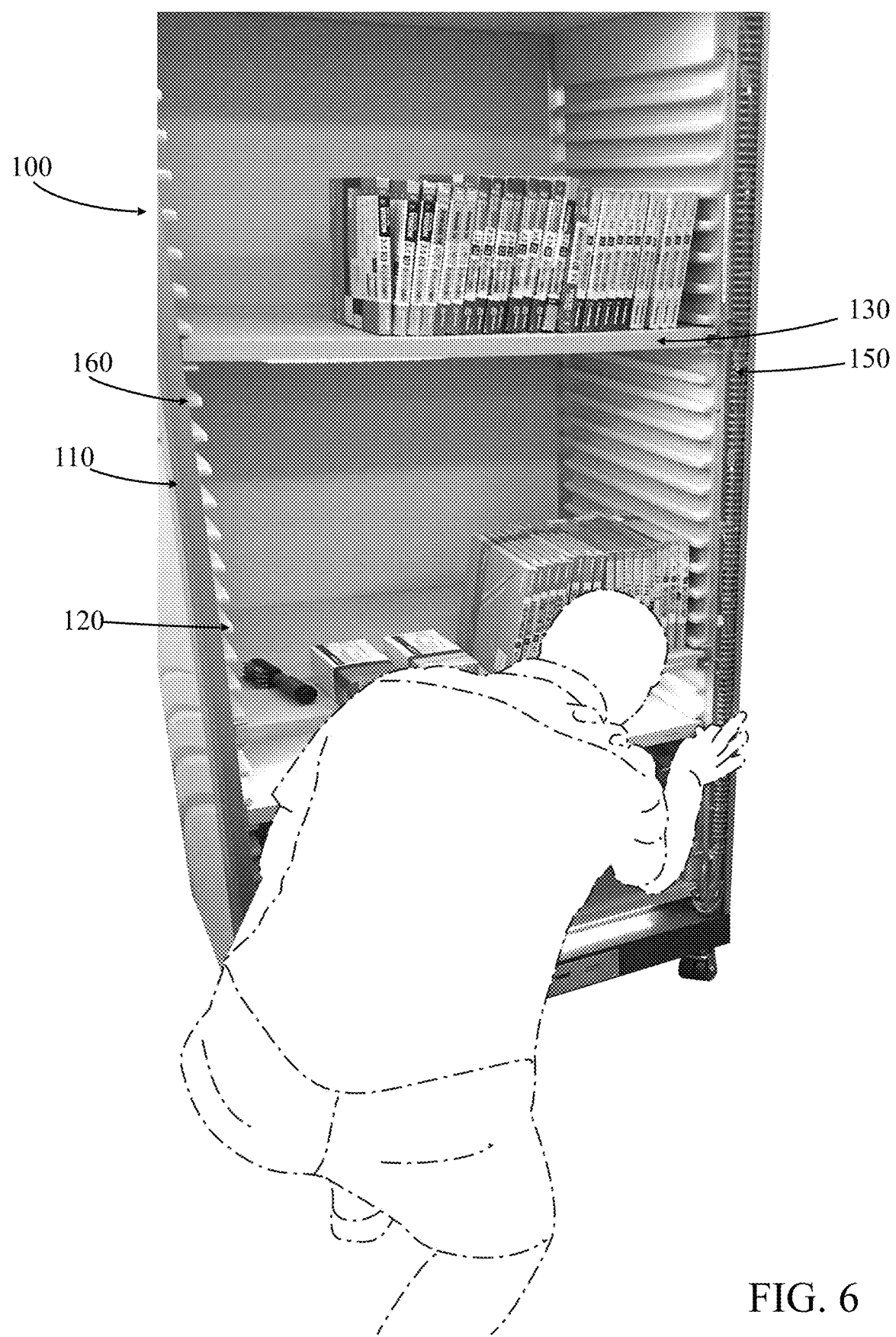
FIG. 6 illustrates various features of an example storage container in accordance with aspects of the present disclosure.

As illustrated in the example implementation of FIG. 6, each of the shelves 130 may be communicatively coupled to a control unit 140 (FIGS. 4 and 5) using a wired coupling 150. For example, the wired coupling 150 may be or include a standard RJ-45 twisted pair Ethernet cable. The RFID signals generated by the reader 142 may be transmitted via one or more of the twisted pairs of the Ethernet cable, and the remaining twisted pairs may be used, for example, to communicate control signals to each of the shelves 130. In order to maintain consistent power and frequency of the signals communicated among the control unit 140 and the shelves 130, the length of each wired coupling 150 may be made constant, regardless of a location of a respective shelf 130 relative to the location of the control unit 140. The use of a constant length for the wired couplings 150 may help control distortion in signals by minimizing electrical variation that would otherwise occur if differing lengths of wired couplings 150 were used (e.g., due to the difference in resistance and other radio frequency effects potentially produced by different lengths of such wired connections).

Additionally, the wired couplings 150 may be connected with the control unit 140 in a specific order, such that the control unit 140 may determine the position of a given shelf relative to the other shelves 130 based on which wired coupling is being used. To achieve this result, each of the wired couplings 150 (for example, 12 separate wired couplings contained in each housing 110) may be attached in a manner that allows for the wired coupling 150 to be connected to shelves 130 only within a limited range of slots 120 in the housing 110. For example, the cable of each wired coupling 150 may be secured to the frame of the storage container 100 or otherwise constrained at a location near an end of the wired coupling 150. By limiting the length of the cable available for connecting the shelf 130 in the housing 110, the position of the shelf 130 may also be constrained. For example, by limiting the distance of the cable secured to the housing, the shelf 130 may be placed in a designated range of distances, which are determined by the length of the cable. A user will thus be provided with limited options regarding placement of the shelf 130 once the shelf is connected to the wired coupling 150. User error relating to the placement of the shelf 130 within the housing may thus be reduced.

In one aspect of the disclosure, to confirm that the shelves 130 are properly ordered (for example, from top to bottom, shelf 1 to shelf 12), the control unit 140 may sequentially illuminate the status light of each shelf (e.g., at the time of installation, rebooting the storage container 100, addition or removal of a shelf, etc.). Each shelf 130 may also or alternatively include a display configured to display a number or other symbol indicative of the shelf's order relative to other shelves as determined by the control unit 140. In one aspect of the disclosure, any shelf 130 may be placed and connected to any wired coupling 150. As described above in relation to the length of the cable, the shelf 130 may be placed within a corresponding slot 120. For example, any shelf 130 may be identified by the system as shelf 1, and the shelf may later be moved and re-attached and identified as shelf 8. Thus, although each shelf 130 may include a specific serial number for tracking and maintenance purposes, any shelf 130 may be placed within any housing 110 and within any slot 120 (based on the constraints of the wired coupling 150, described above). The discovery and enumeration process of the connected shelves to the wired couplings 150 may also occur, for example, at the time of installation, rebooting the storage container 100, addition or removal of a shelf, etc. Upon the discovery and enumeration process, the control unit 140 may transmit a signal (for example, the quantity of the shelves 130 connected to the wired couplings 150, the placement of the shelves within the housing 110, serial numbers, etc.) to inventory management system 1120 indicating the identity and arrangement of the storage container 100.

In another aspect of the disclosure, although the housing 110 may contain a plurality of wired couplings 150 (e.g., 12 wired couplings), not all of the wired couplings may be connected to a shelf, that is, not all couplings must be used. Thus, the numbering arrangement of the shelf 130 within the housing 110 may be determined by the total number of overall connected shelves. For example, wired coupling 150, labeled from 1-12 may only have shelves 130 attached at even connections (i.e., 2, 4, 6, 8, 10, 12). Thus, shelves placed at wired couplings 2, 4, 6, 8, 10 and 12 may be recognized by the control unit 140 as shelves 1, 2, 3, 4, 5, 6, respectively.

To adjust the location of the shelves 130, the storage container 100 may include one or more removable faceplates 160 that conceal the wired couplings 150. The removable faceplates 160 may be removed using, for example, a hex screwdriver and/or other features that may discourage ready access by unauthorized personnel.

Figure 13:
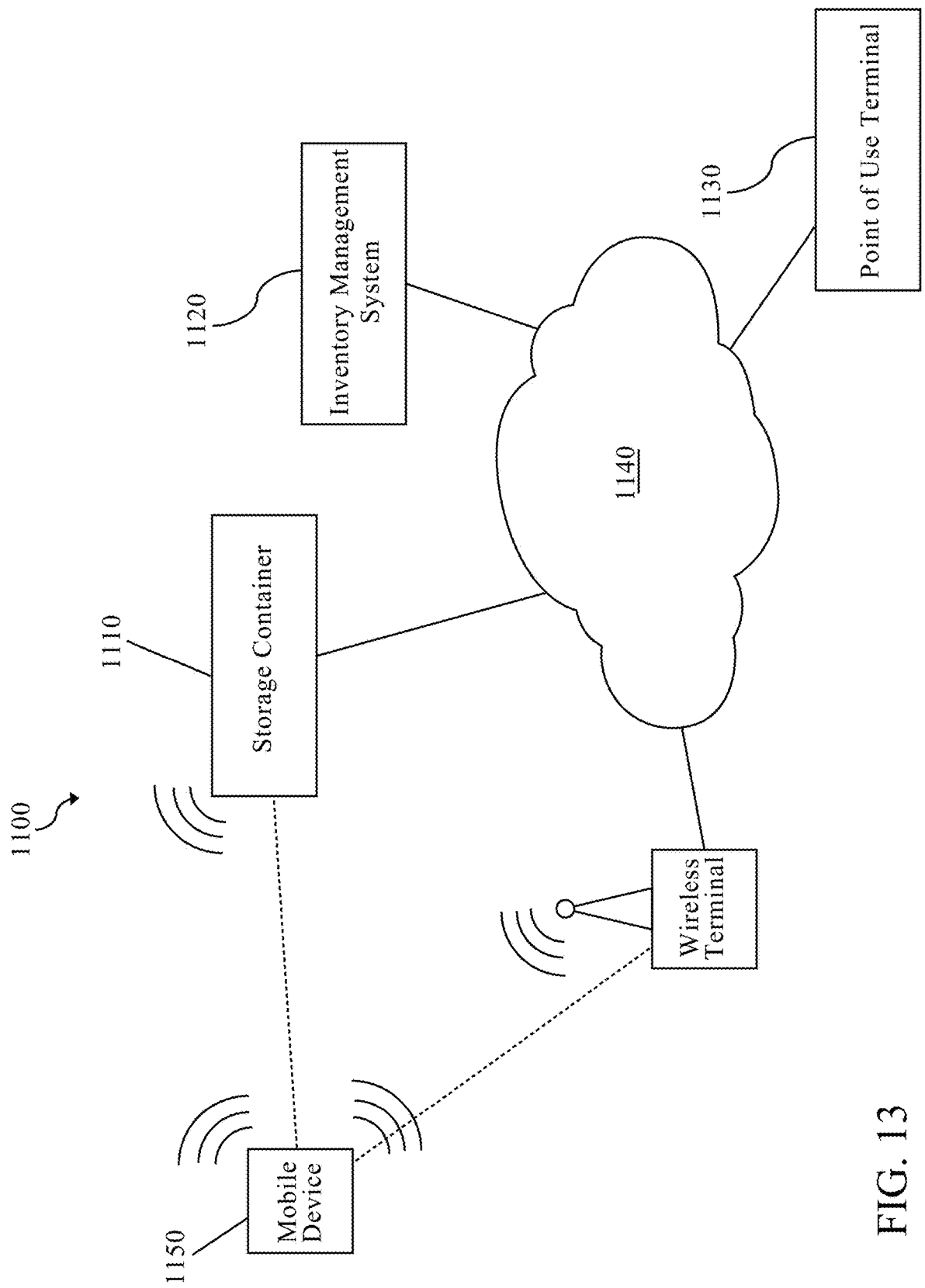
FIG. 13 illustrates various features for an example network for managing inventory in accordance with aspects of the present disclosure.

To troubleshoot/repair the storage container, the control unit 140 may include a communication module 148, as illustrated in FIG. 5, for communicating with an external device in proximity to the storage container 100, such as a laptop or mobile device 1150 (FIG. 13). The communication module 148 may include a wired connector, such as an Ethernet or universal serial bus (USB) connector, and/or the communication module may include a wireless network adapter for communicating with a mobile or other device wirelessly, such as via a Bluetooth, Wi-Fi, or NFC connection (see, e.g., U.S. patent application Ser. No. 15/455,065, filed on Mar. 9, 2017, now issued U.S. Pat. No. 10,115,073, the contents of which are hereby incorporated in their entirety herein by reference). In this way, a technician may readily configure the storage container 100 (FIG. 1) for operation, obtain diagnostic information for help with identifying any issues with proper operation of the storage container 100 (FIG. 1), and/or carry out operations to repair the storage container 100 (FIG. 1). Alternatively, or additionally, the control unit 140 may communicate diagnostic information via a remote server over a network, such that the technician may attempt to resolve any operational issues remotely or prepare to resolve such issues upon accessing the device locally. The control unit 140 may also optionally, for example, cause the status light 132 (FIG. 1) to illuminate in order to identify a shelf in need of repair, replacement, or other service.

Figure 7:
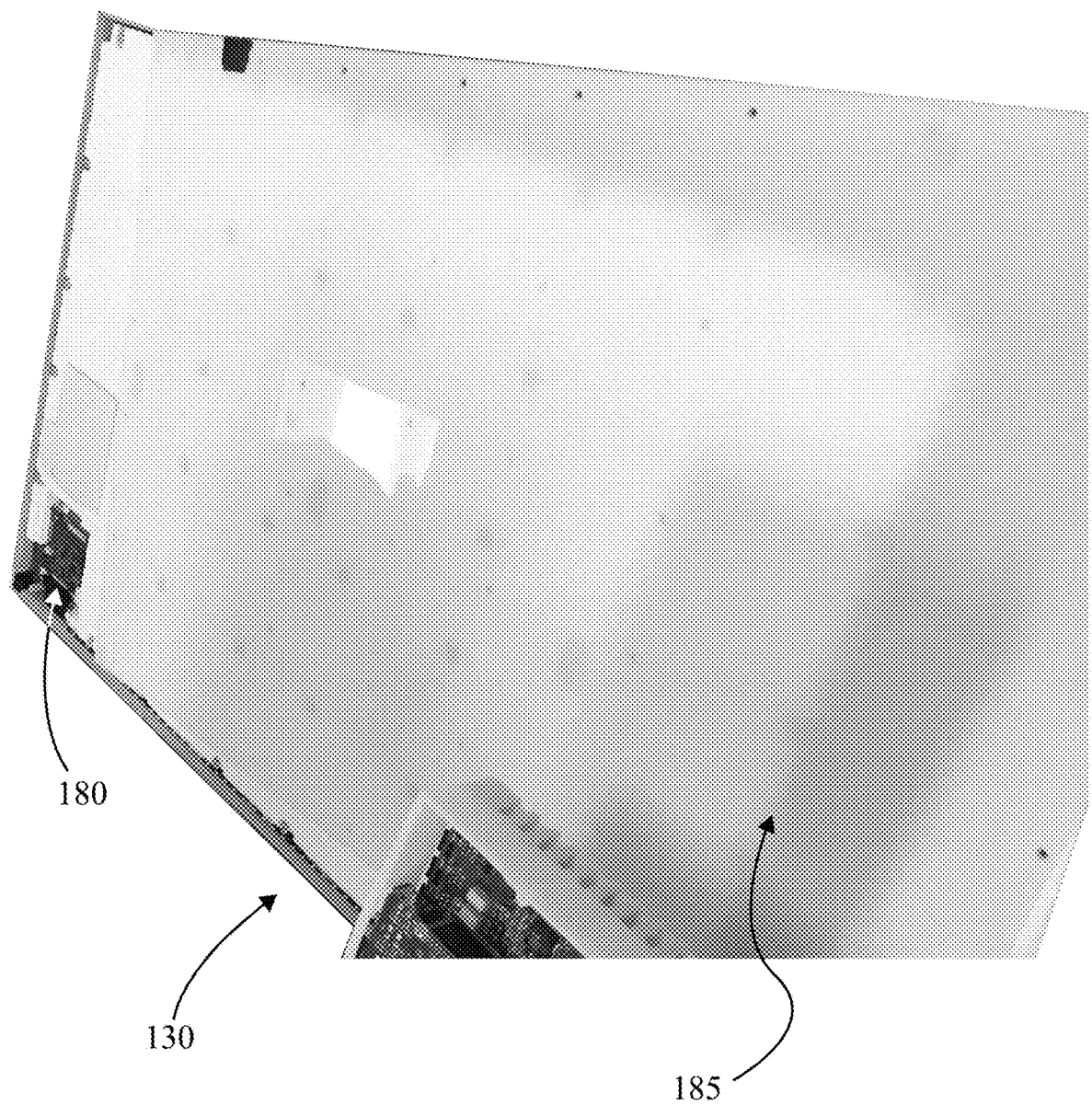
FIGS. 7 and 8 illustrate internal views of various features of one example implementation of shelves of an example storage container, including a shelf-located controller, in accordance with aspects of the present disclosure.
Figure 8:
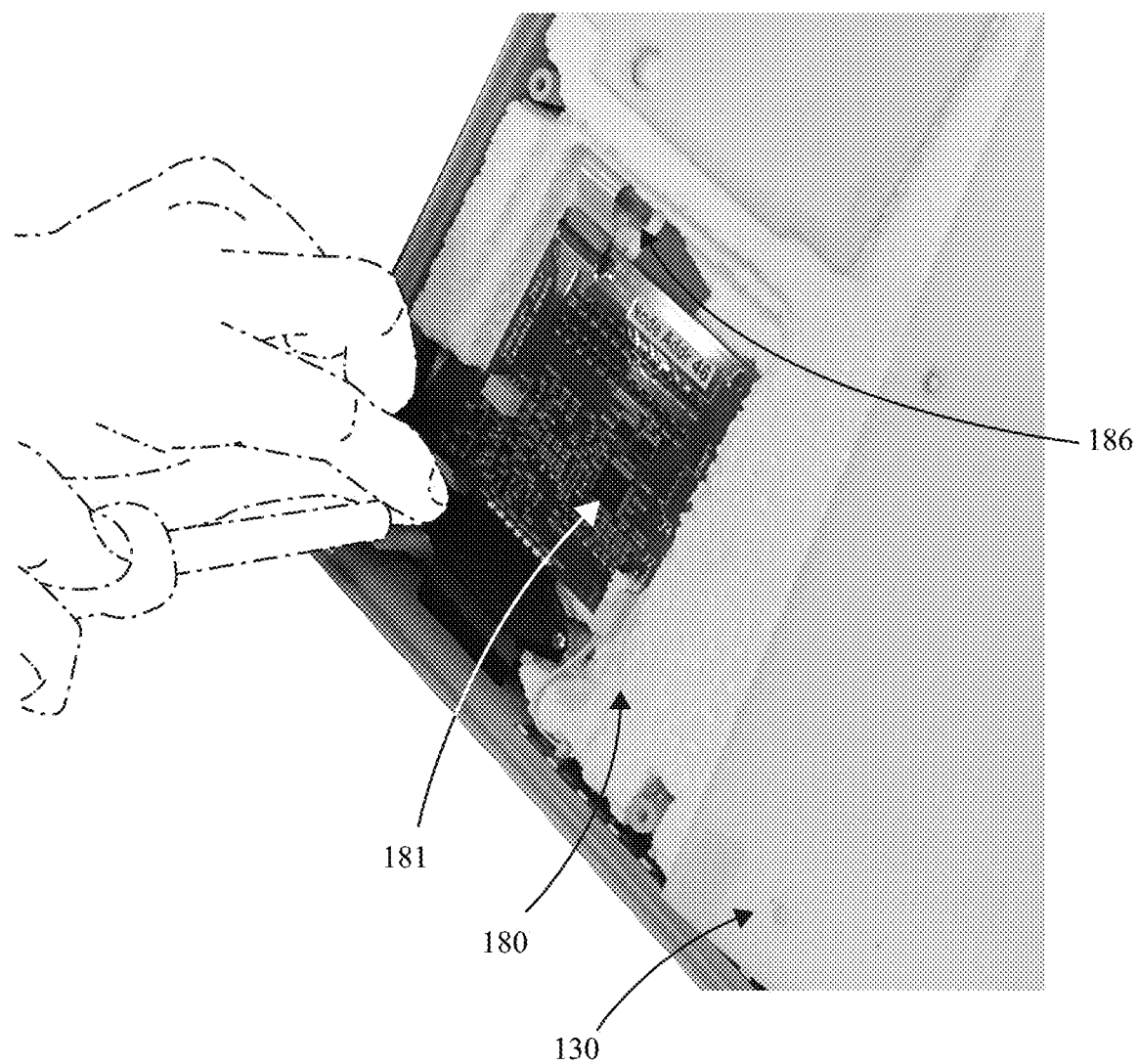
Figure 9:
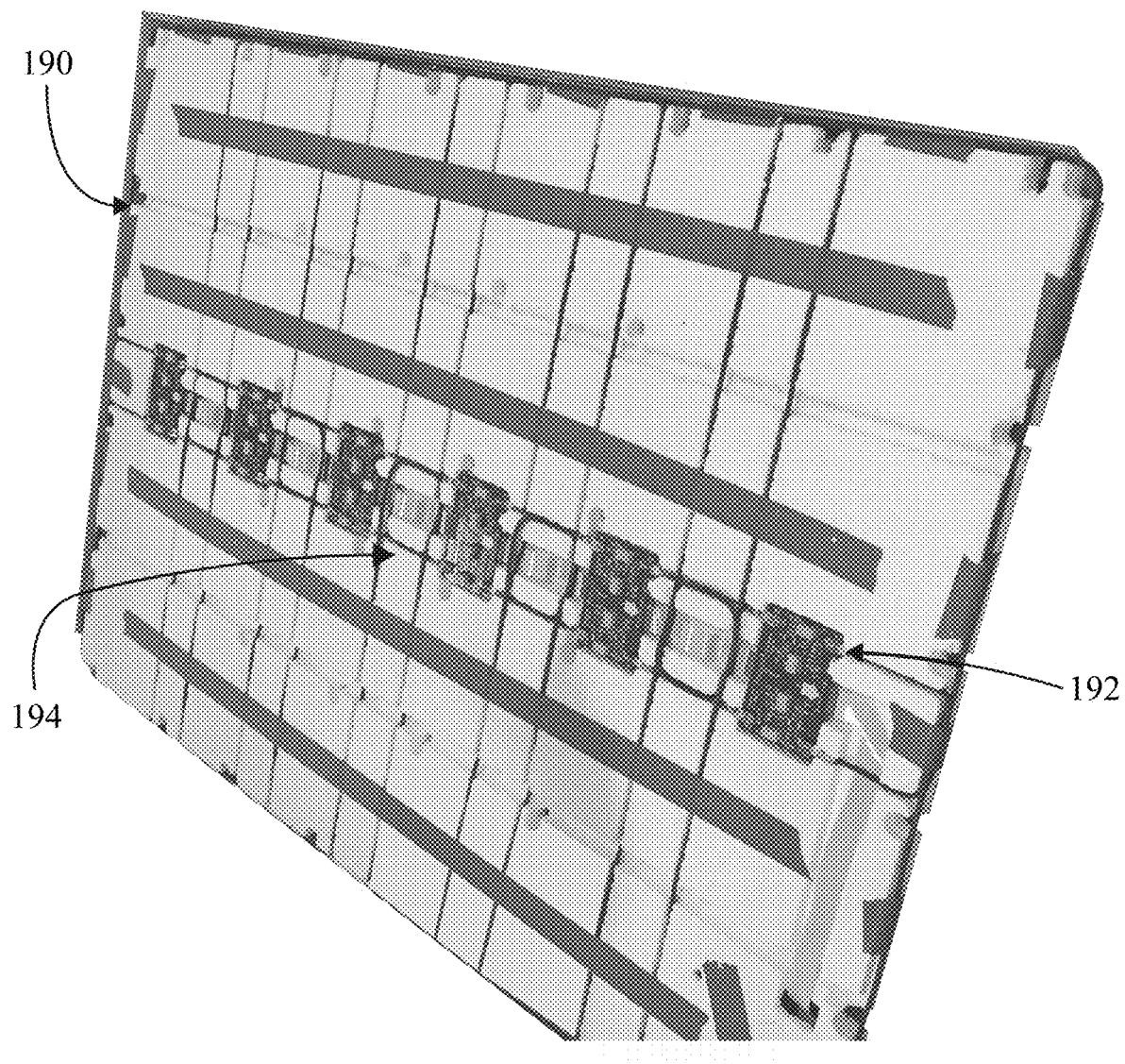
FIGS. 9-10 illustrate an example antenna circuit of one of the shelves of an example storage container in accordance with aspects of the present disclosure.
Figure 10:
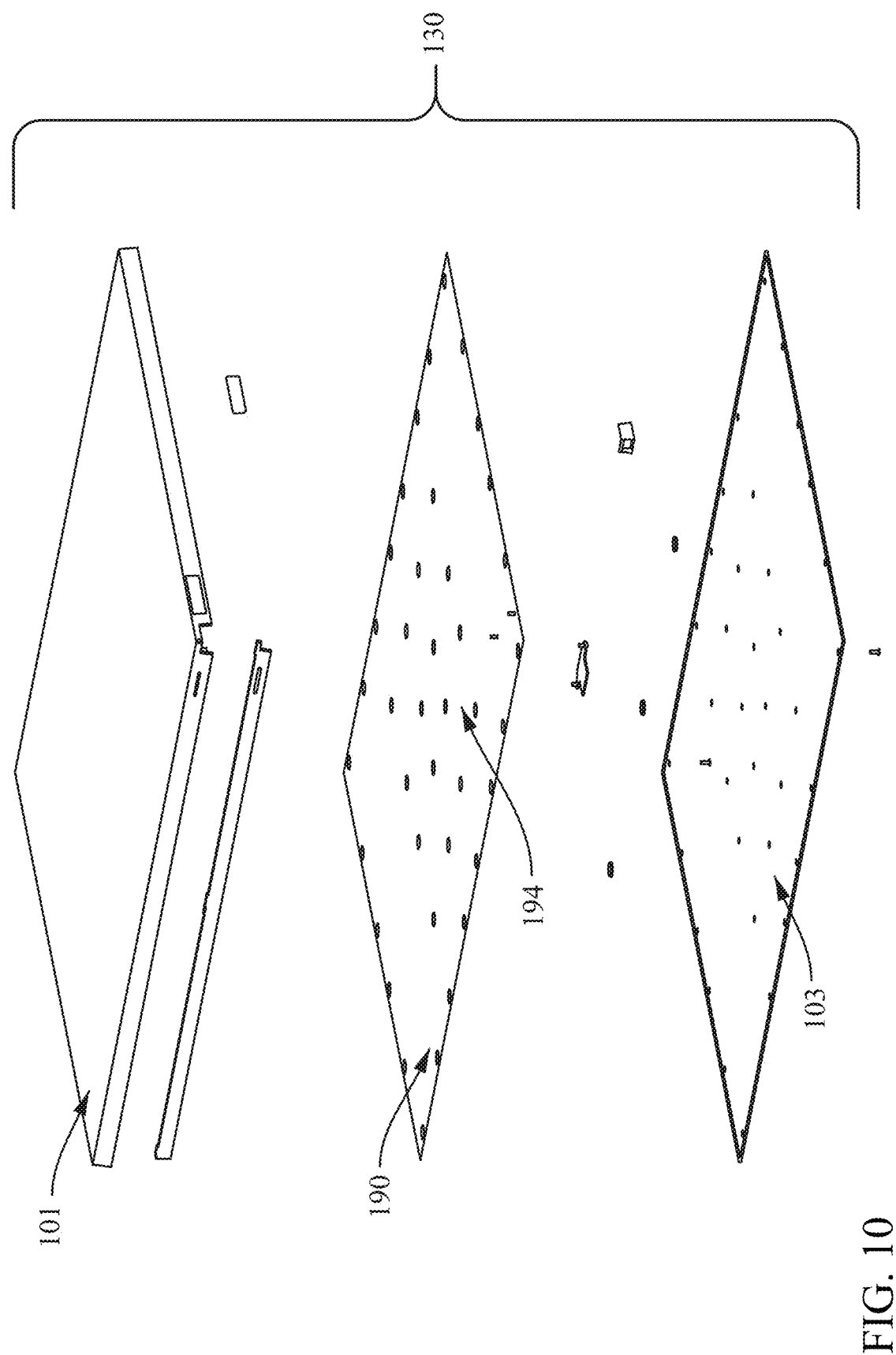

Referring to the example aspect of the disclosure as illustrated in FIGS. 7-12, each shelf 130 may include an array of antennas 190 and a shelf-located controller 180 for communicating with the control unit 140 and for controlling the array of antennas 190, for example. The shelf-located controller 180 may be coupled to the control unit 140 via wired coupling 150 and may also be coupled via wired or wireless connectivity 186 to one or more antenna circuits 192 of the shelf 130. Alternatively, as illustrated in FIG. 10, the one or more antenna circuits 192 may be combined within a single circuit within a single circuit board. Each antenna circuit 192, or the single antenna circuit, may be coupled to one or more antenna loops 194 of the array of antennas 190, as illustrated in FIG. 9. Alternatively, as illustrated in FIG. 10, the one or more physical antenna loops 194 of FIG. 9, may be replaced by copper traces onto a single circuit board for example. The shelf-located controller 180 may be configured to communicate the RFID signals generated by the reader 142 to each antenna circuit 192. The antenna circuits 192 may be powered via the wired connection 186 to the shelf-located controller 180, which in turn may receive power from the control unit 140 via wired coupling 150. Alternatively, the shelf-located controller 180 may be powered by a separate external power supply or a separate internal power source, such as a battery.

Figure 11:
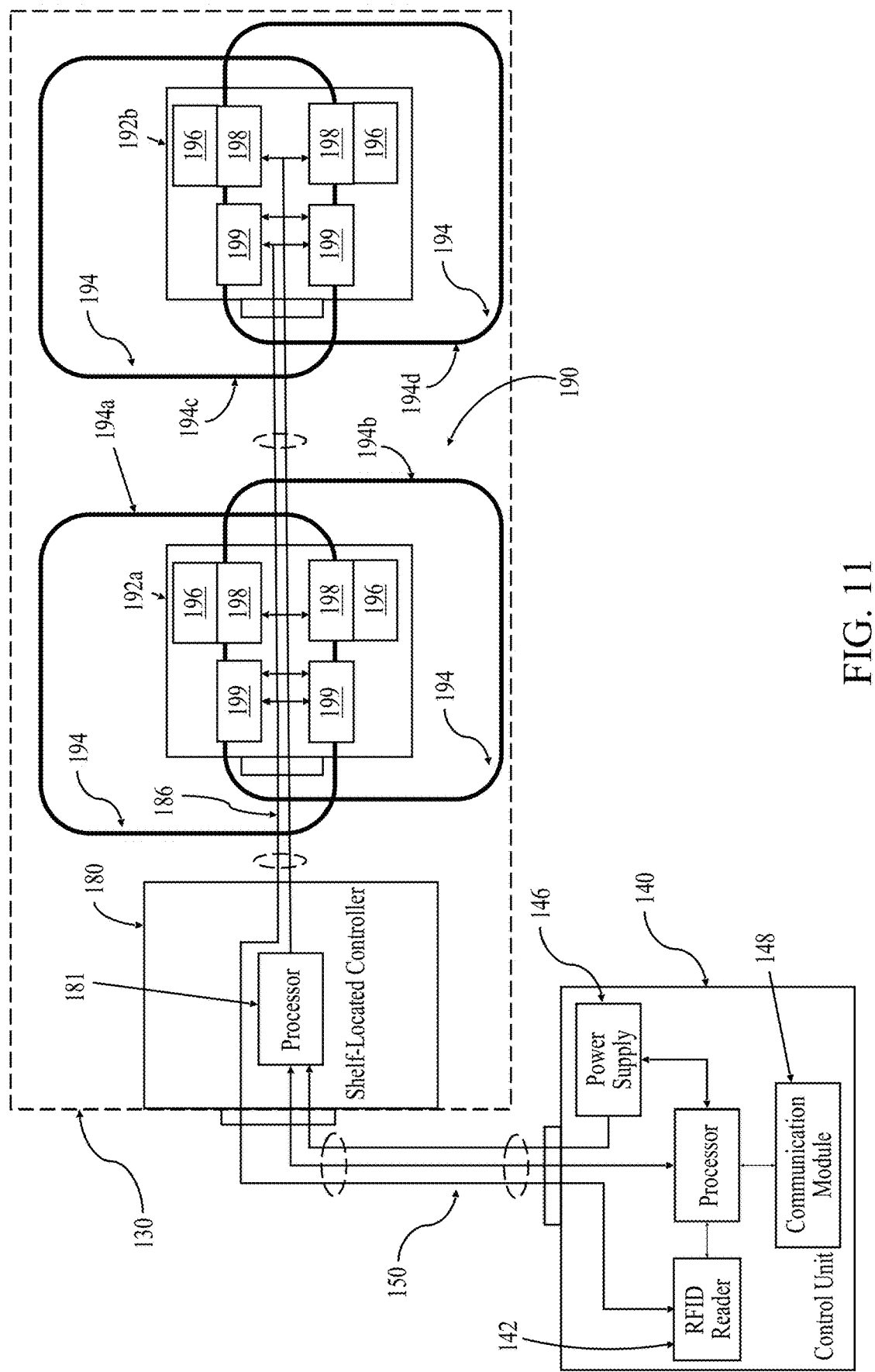
FIGS. 11-12 illustrate an example arrangement of various components of an example storage container in accordance with aspects of the present disclosure.
Figure 12:
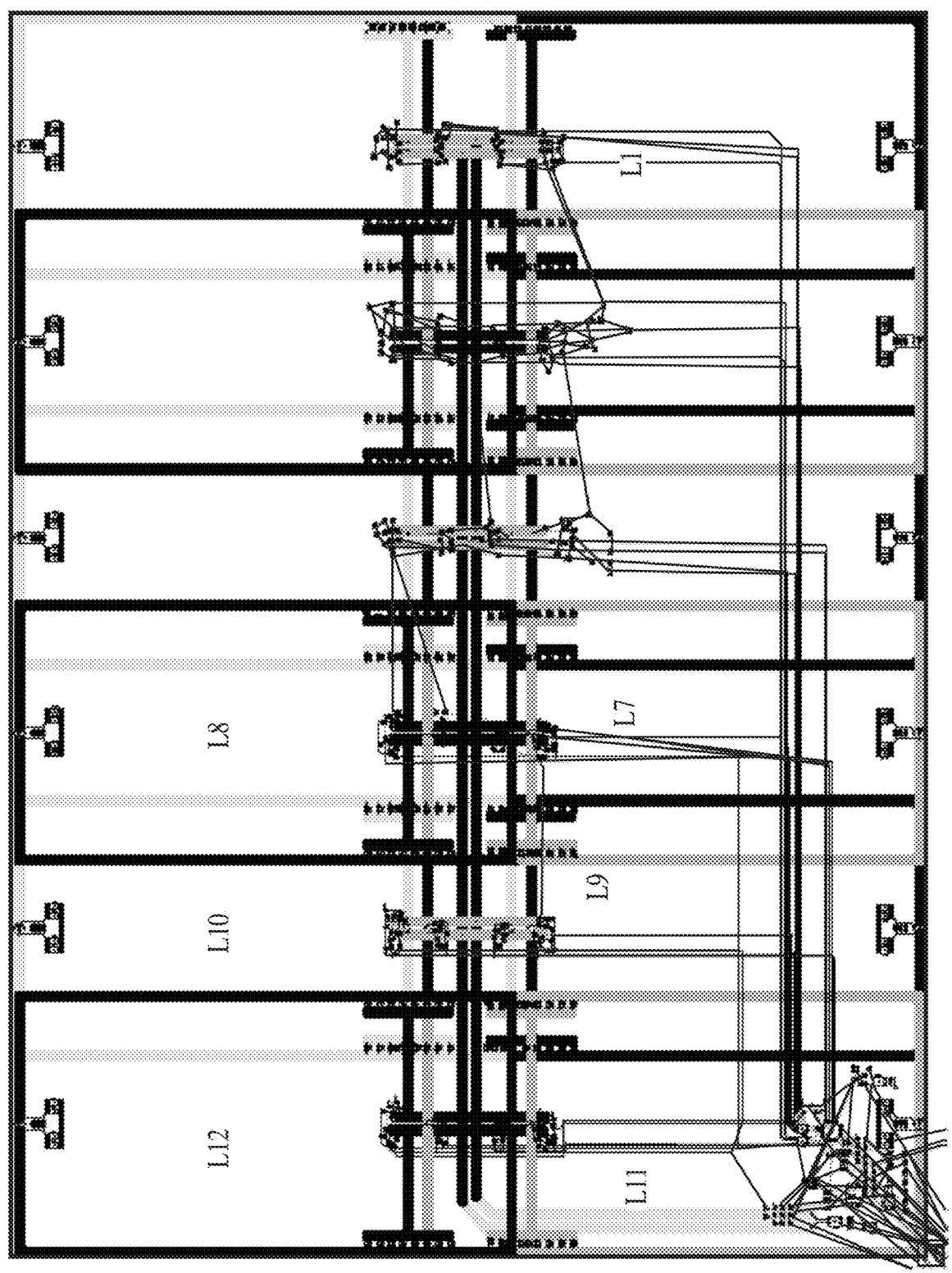

Referring to FIG. 11, each antenna circuit 192 may be coupled to two antenna loops 194. Each antenna circuit 192 may include one or more tuning circuits 196 configured to tune each connected antenna loop 194 to an appropriate frequency for reading corresponding RFID tags. Each antenna circuit 192 may also include one or more tuning relays 198 configured, for example, to: (i) couple the associated antenna loop 194 with the tuning circuit 196 to tune each antenna loop 194 to the desired frequency; or (ii) de-couple the associated antenna loop 194 from the tuning circuit 196, such that the associated antenna loop 194 is an open circuit that does not substantially interfere with RF emitted via operating antenna loops of the array. Each antenna circuit 192 may also include one or more signal relays 199 configured to either power-on the associated antenna loop 194 by connecting the antenna loop 194 with the RFID signals generated by the reader 142 or power-off the associated antenna loop 194 by disconnecting the antenna loop 194 from the RFID signals, which are generated by the reader 142 transmitted via the wired coupling 150 to the shelf-located controller 180 and via wired connection 186 to the antenna circuits 192.

The shelf-located controller 180 may include a processor 181 for processing communications from the control unit 140 and for controlling the tuning relays 198 and signal relays 199 of the antenna circuit 192. For example, the shelf-located controller 180 may receive instructions from the control unit 140 via the wired coupling 150. Based on the received instructions, the shelf-located controller 180 may initiate a read cycle in which the shelf-located controller 180 may control the relays 198, 199 via wired connection 186 to cause each antenna loop 194 to connect with the tuning circuit 196 and power-on to read nearby RFID tags, then power-off and detune in a sequential manner, such that each antenna loop 194 of the array of antennas 190 is tuned and powered-on to read nearby RFID tags while the other antenna loops 194 are detuned and disconnected from the RFID signals generated by the reader 142. In various aspects of the disclosure, one or more of the antenna loops 194 may be disconnected from the RFID signals, but may remain tuned (i.e., connected to the tuning circuit 196), in a manner so as to alter the electromagnetic field of a nearby antenna loop while the nearby antenna loop is tuned and powered for a read cycle. In various aspects, more than one antenna loop 194 of the array of antennas 190 may be tuned contemporaneously. In various aspects, one or more antenna loops of different shelves 130 may be tuned sequentially and/or contemporaneously in any desired combination or sequence. In various aspects, one or more antenna loops of different shelves 130 may powered-on sequentially in any desired combination or sequence.

In various aspects of the present disclosure, as illustrated in FIGS. 9-12, each antenna loop 194 may be generally oriented along a horizontal plane. A portion of the loop of each antenna loop 194 may overlap a portion of the loop of one or more of the other antenna loops 194 of the array of antennas 190. Due to the overlapping antenna loops 194, the resulting aggregate coverage of the field or signal emitted from the antenna loops 194 may be improved. In addition, the antenna loops 194 may be powered according to a specified pattern. For example, in one aspect of the disclosure, a first antenna loop 194*a* may be tuned and powered-on to obtain signals from RFID tags within the electromagnetic field emitted by the first antenna loop 194*a*. After powering-off the first antenna loop 194*a*, an adjacent second antenna loop 194*b* may be tuned and powered-on to obtain signals from RFID tags within the electromagnetic field emitted by the second antenna loop 194*b*. Since the spatial area of the electromagnetic field of the first antenna loop 194*a* overlaps the spatial area of the electromagnetic field of the second antenna loop 194*b*, if an RFID tag is positioned and oriented in a "dead spot" such that the electromagnetic field of the first antenna loop 194*a* has a low probability of reading the tag, then it is unlikely that the tag will also be in a "dead spot" of the electromagnetic field of the second antenna loop 194*b*. Of course, in this arrangement, certain RFID tags will be read by multiple antenna loops 194, but the control unit 140 or inventory management system 1120 may be equipped with appropriate hardware and/or software to identify and eliminate duplicate reads.

As further illustrated in FIGS. 7 and 8, each antenna loop 194 of the array of antennas 190 may be formed from or include conductive wire and may be positioned in a channel formed in a layer of material interposed between upper and lower surfaces of the shelf 130. Each shelf 130 may also include an insulation layer 185 covering the array of antennas 190.

Alternatively, as illustrated in FIG. 10, an insulation layer may not be needed based upon the single circuit board implementation. In one aspect of the disclosure, and as further illustrated in FIGS. 10 and 12, the antenna loops 194, along with the additional elements described in conjunction with shelves 130 of FIG. 11 as described above, may be printed on a single circuit board or other substrate. For example, all of the PCBs, cabling and RF Loop wires as referenced in conjunction with shelves 130 of FIG. 11, may be combined into a single board. The single circuit board comprising each respective shelf 130, may be roughly 24"×30", for example. The single circuit board may be positioned in a channel formed in a layer of material interposed between upper surface 101 and lower surface 103 of the shelf 130.

In various aspects, one or more antenna loops 194 may be oriented along planes that are approximately orthogonal to or oblique to the other antenna loops 194 of the array of antennas 190. Moreover, one or more additional arrays of antennas may be oriented along approximately orthogonal or oblique planes with respect to the other arrays of antennas of the storage container. In this manner, "dead spots" in or near the storage container may be reduced or eliminated. In use, for example, the control unit 140 (FIG. 11). may transmit a high frequency (HF) signal to one or more of the shelves 130 (FIG. 1), such as at a frequency between approximately 3 and 36 megahertz (MHz). In another example implementation, the control unit 140 may transmit an UHF signal (e.g., at, near, or via one or more of the shelves or at another location in the storage container), such as at a frequency between approximately 300 MHz and 3 GHz. In another example implementation, the control unit 140 may transmit a LF signal at a frequency between approximately 30 kHz and 300 kHz, for example. In yet another example implementation, the control unit 140 may also include an attenuator for selectively reducing the power of the signal communicated with the shelves 130. For example, the nominal power may be about 1 to 5 Watts, and the attenuator may reduce the power to about 25% of the nominal power for a subsequent read cycle. By reducing the power selectively, the control unit 140 may be used to more accurately determine the location of a given product. For example, the reduced power may result in RFID tags being identified only by one or more antenna loops that are typically in closest proximity to each RFID tag. In some instances, each shelf 130 (FIG. 1) may be equipped with one or more calibration RFID tags (not shown) affixed to the shelf. The calibration RFID tags, among other things, may be used to confirm proper operation of each of the antenna loops, the presence of a shelf in proximity to the other shelves, and/or the location of a shelf relative to the other shelves.

By adjusting the power level of the signals transmitted to the shelves 130, of FIG. 1, for example, various features of the storage container 100 may be used determine or estimate a location of a given product. For example, the power level of the transmitted signal may be increased and/or decreased to determine a threshold readability of RFID tags proximal to each shelf or portion of each shelf (e.g., to assist in confirming and/or inferring the location of each product having an RFID tag attached thereto). In further implementations, by sequentially tuning and powering-on each of the antenna loops and/or by adjusting the power level of the transmitted signals, various features of the storage container 100 may be used to determine a location of a given product based on which antenna loop detected a response from the RFID tags and/or relative signal strength. For example, if a plurality of antenna loops each detect a response from the RFID tag, the power level of the transmitted signal for each antenna loop may be selectively reduced to narrow down which antenna loop(s) detect a response at differing power levels, in order to determine the likely location of the product; for example, the product may be located on a shelf nearest the antenna loop that detected the product at the lowest transmitted signal level. In this way, various features of the storage container 100 may be used to resolve multiple "claims" to an RFID tag when the same tag is read by more than one antenna loop.

Furthermore, by using individual antenna loops arranged in a specified pattern, a depth within the shelf of (and/or distance to) the detected product may be determined or estimated. For example, if a first loop of a pair of antennas is positioned toward a front portion of the shelf and detects a response from an RFID tag, the second loop positioned toward a back portion of the shelf does not detect a response from the RFID tag, the product may be determined to be likely located toward the front portion of the shelf (or vice-versa). Thus, the depth on shelf location of the product may be more accurately determined based on which antenna loop detected a response from the RFID tag. Moreover, information gathered from antennas of other nearby shelves may be used to help resolve whether the product is located above or below a particular shelf. This location information may be used, for example, to further signal to a user the location of the inventory item (e.g., by lighting a portion of the shelf, such as front or rear, corresponding to the identified or estimated location).

Figure 14:
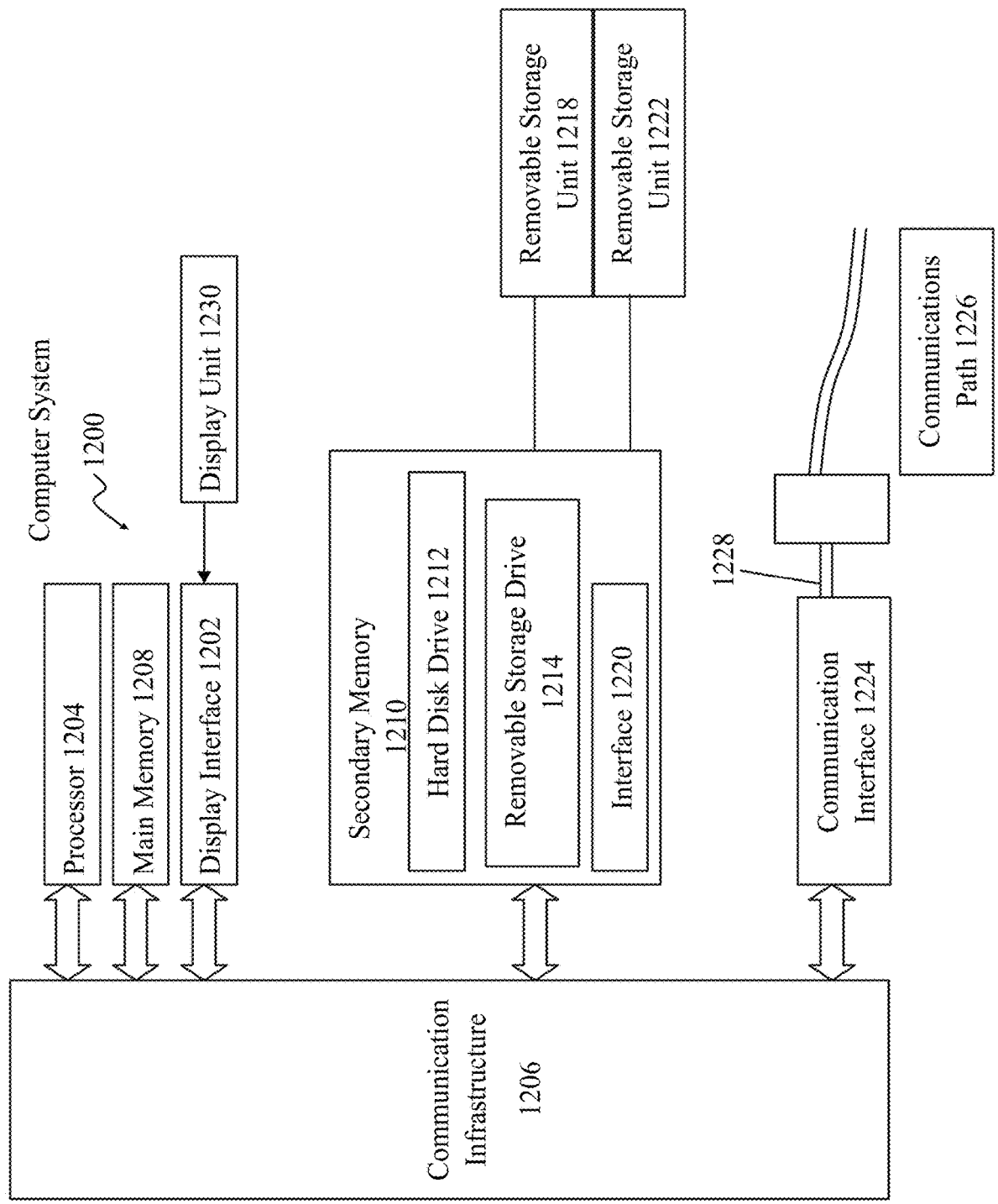
FIG. 14 illustrates various features of an example computer system for use in conjunction with aspects of the present disclosure.

FIG. 13 illustrates various features in an example system 1100 for managing inventory in accordance with aspects of the present disclosure. For example, system 1100 may include a storage container 1110 (e.g., the storage container 100 of FIG. 1), an inventory management system 1120, and a point of use terminal 1130, each coupled to one another via a network 1140. The system 1100 may also include a terminal 1150, such as a mobile device, that may be selectively communicatively coupled with the storage container 1110 via wireless connection. The mobile device 1150 may also be selectively communicatively coupled with the network 1140 via a wireless connection with another terminal 1160 coupled to the network 1140. For example, network 1140 may be used to facilitate communications among multiple systems, including the storage container 1110, the inventory management system 1120, the point of use terminal 1130, and the terminal 1150. In some implementations, the network 1140 may include the Internet or another Internet Protocol (IP) based network. The storage container 1110, the inventory management system 1120, and/or the point of use terminal 1130 may include one or more computer systems, which may include one or more terminals having various features as shown in FIG. 14 and described in conjunction therewith. In some implementations, the inventory management system 1120 may also include a memory that stores instructions for executing processes for managing inventory, and a processor configured to execute the instructions.

In some implementations, the storage container 1110 may identify and check inventory stored thereon and provide such information to the inventory management system 1120. Additionally, the storage container 1110 may also determine when a product is no longer detected within its inventory and may notify the inventory management system 1120 accordingly. Using this information, the inventory management system 1120 may monitor one or more point of use terminals 1130 to determine whether the undetected product has been used by a technician, medical professional, etc., at one or more of the point of use terminals 1130. For example, the RFID tag applied to a product may be scanned to provide for a final disposition at a point-of-sale, a point-of-use, a trash receptacle, or any other instance when the individual product is removed from inventory, and the one or more point of use terminals 1130 may report such disposition to the inventory management system 1120. Such operations may, for example, include one or more operations described in U.S. patent application Ser. No. 11/765,950, filed on Jun. 20, 2007, now issued as U.S. Pat. No. 8,281,994, described in U.S. patent application Ser. No. 11/383,422, filed on May 15, 2006, now issued as U.S. Pat. No. 7,639,136, and/or described in U.S. patent application Ser. No. 12/616,630, filed on Nov. 11, 2009, now issued as U.S. Pat. No. 7,990,272, the contents of each of which is hereby incorporated by reference in its entirety. As result, a determination may be made by the inventory management system 1120 whether the undetected product has been used or is missing from the overall inventory, such as may result as part of an effort to resolve inventory discrepancies and/or update inventory. Additionally, while the products are stored in the storage container 1110, information related to such products may be transmitted to the inventory management system 1120. In this way, the inventory management system 1120 may monitor each of the products stored by the storage container 1110 to determine whether there are missing products, expired products, and/or products near expiration, for example. Additionally, the inventory management system 1120 may use this information to, for example, predict inventory needs based on use history and maintain age and other data for inventory items (e.g., to identify expired or out of date items). In some aspects, various functions, such as reconciling which shelf the product is located on, may be performed locally by various components and processors within the storage container 1110 or may be performed remotely, for example, via the inventory management system 1120.

Aspects of the present disclosure may be implemented using hardware, software, or a combination thereof and may be implemented in one or more computer systems or other processing systems. In an aspect of the present disclosure, features are directed toward one or more computer systems capable of carrying out the functionality described herein. An example of such a computer system 1200 is shown in FIG. 14.

Computer system 1200 includes one or more processors, such as processor 1204. The processor 1204 is connected to a communication infrastructure 1206 (e.g., a communications bus, cross-over bar, or network). Various software implementations are described in terms of this example computer system. After reading this description, it will become apparent to a person skilled in the relevant art(s) how to implement implementations of the disclosure using other computer systems and/or architectures.

Computer system 1200 may include a display interface 1202 that forwards graphics, text, and other data from the communication infrastructure 1206 (or from a frame buffer not shown) for display on a display unit 1280. Computer system 1200 also includes a main memory 1208, preferably random access memory (RAM), and may also include a secondary memory 1210. The secondary memory 1210 may include, for example, a hard disk drive 1212, and/or a removable storage drive 1214, representing a floppy disk drive, a magnetic tape drive, an optical disk drive, a universal serial bus (USB) flash drive, etc. The removable storage drive 1214 reads from and/or writes to a removable storage unit 1218 in a well-known manner. Removable storage unit 1218 represents a floppy disk, magnetic tape, optical disk, USB flash drive etc., which is read by and written to removable storage drive 1214. As will be appreciated, the removable storage unit 1218 includes a computer usable storage medium having stored therein computer software and/or data.

Alternative implementations of the present disclosure may include secondary memory 1210 and may include other similar devices for allowing computer programs or other instructions to be loaded into computer system 1200. Such devices may include, for example, a removable storage unit 1222 and an interface 1220. Examples of such may include a program cartridge and cartridge interface (such as that found in video game devices), a removable memory chip (such as an erasable programmable read only memory (EPROM), or programmable read only memory (PROM)) and associated socket, and other removable storage units 1222 and interfaces 1220, which allow software and data to be transferred from the removable storage unit 1222 to computer system 1200.

Computer system 1200 may also include a communications interface 1224. Communications interface 1224 allows software and data to be transferred between computer system 1200 and external devices. Examples of communications interface 1224 may include a modem, a network interface (such as an Ethernet card), a communications port, a Personal Computer Memory Card International Association (PCMCIA) slot and card, etc. Software and data transferred via communications interface 1224 are in the form of signals 1228, which may be electronic, electromagnetic, optical or other signals capable of being received by communications interface 1224. These signals 1228 are provided to communications interface 1224 via a communications path (e.g., channel) 1226. This path 1226 carries signals 1228 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage unit 1218, a hard disk installed in hard disk drive 1212, and signals 1228. These computer program products provide software to the computer system 1200. Implementations of the present disclosure are directed to such computer program products.

Computer programs (also referred to as computer control logic) are stored in main memory 1208 and/or secondary memory 1210. Computer programs may also be received via communications interface 1224. Such computer programs, when executed, enable the computer system 1200 to perform the features in accordance with implementations of the present disclosure, as discussed herein. In particular, the computer programs, when executed, enable the processor 1204 to perform the features in accordance with implementations of the present disclosure. Accordingly, such computer programs represent controllers of the computer system 1200.

In an aspect of the present disclosure where the disclosure is implemented using software, the software may be stored in a computer program product and loaded into computer system 1200 using removable storage drive 1214, hard drive 1212, or communications interface 1220. The control logic (software), when executed by the processor 1204, causes the processor 1204 to perform the functions described herein. In another aspect of the present disclosure, the system is implemented primarily in hardware using, for example, hardware components, such as application specific integrated circuits (ASICs). Implementation of the hardware state machine to perform the functions described herein will be apparent to persons skilled in the relevant art(s).

Figure 15A:
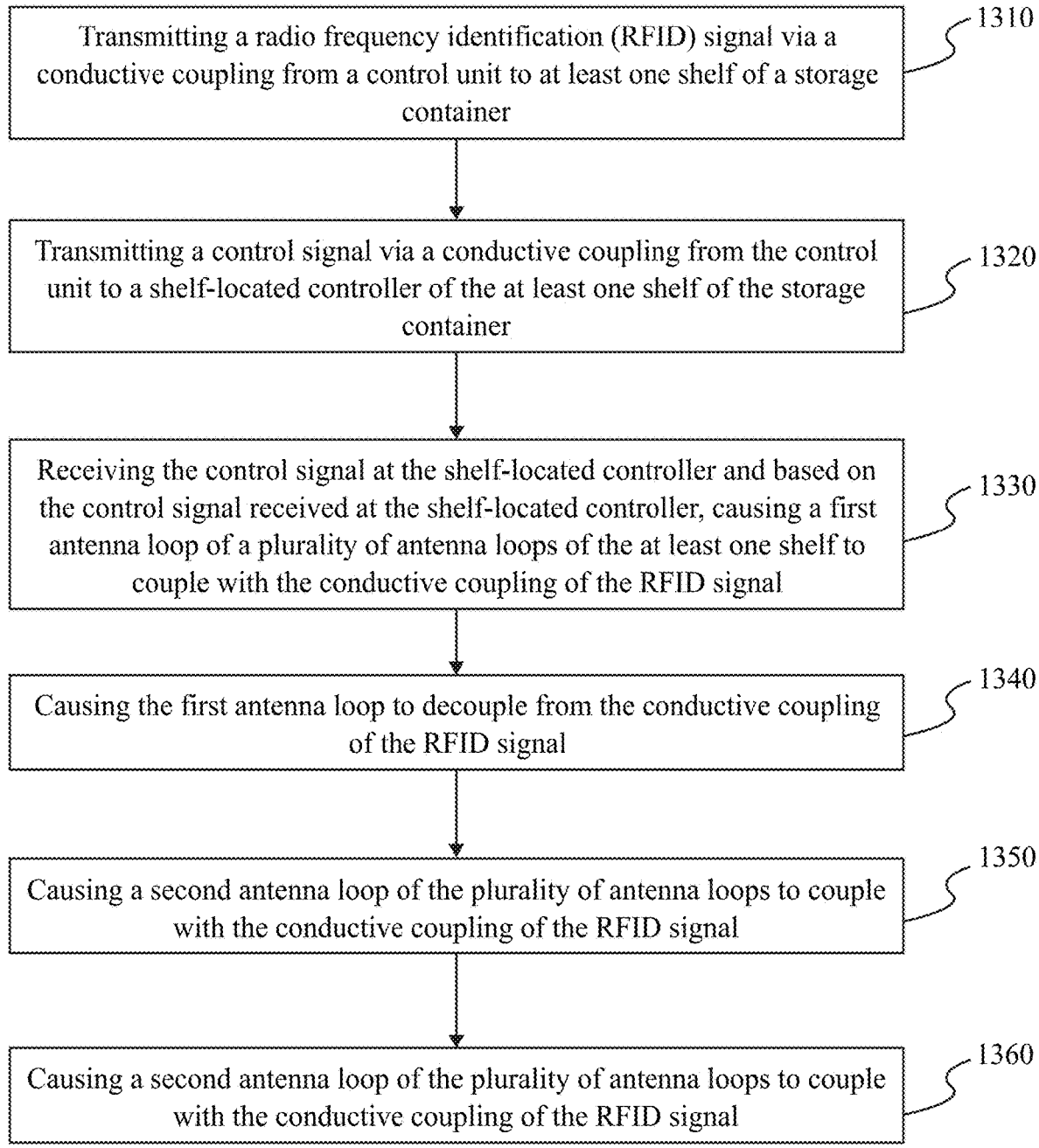
FIGS. 15A and 15B illustrate an example flowchart for managing inventory in accordance with aspects of the present disclosure.

FIG. 15A illustrates an example method for managing inventory in accordance with aspects of the present disclosure. The method includes transmitting a radio frequency identification (RFID) signal via a conductive coupling from a control unit to at least one shelf of a storage container 1310. The method further includes transmitting a control signal via a conductive coupling from the control unit to a shelf-located controller of the at least one shelf of the storage container 1320. The method also includes receiving the control signal at the shelf-located controller and based on the control signal received at the shelf-located controller, and causing a first antenna loop of a plurality of antenna loops of the at least one shelf to couple with the conductive coupling of the RFID signal 1330. The method also includes causing the first antenna loop to decouple from the conductive coupling of the RFID signal 1340, causing a second antenna loop of the plurality of antenna loops to couple with the conductive coupling of the RFID signal 1350, and causing the second antenna loop to decouple from the conductive coupling of the RFID signal 1360.

Figure 15B:
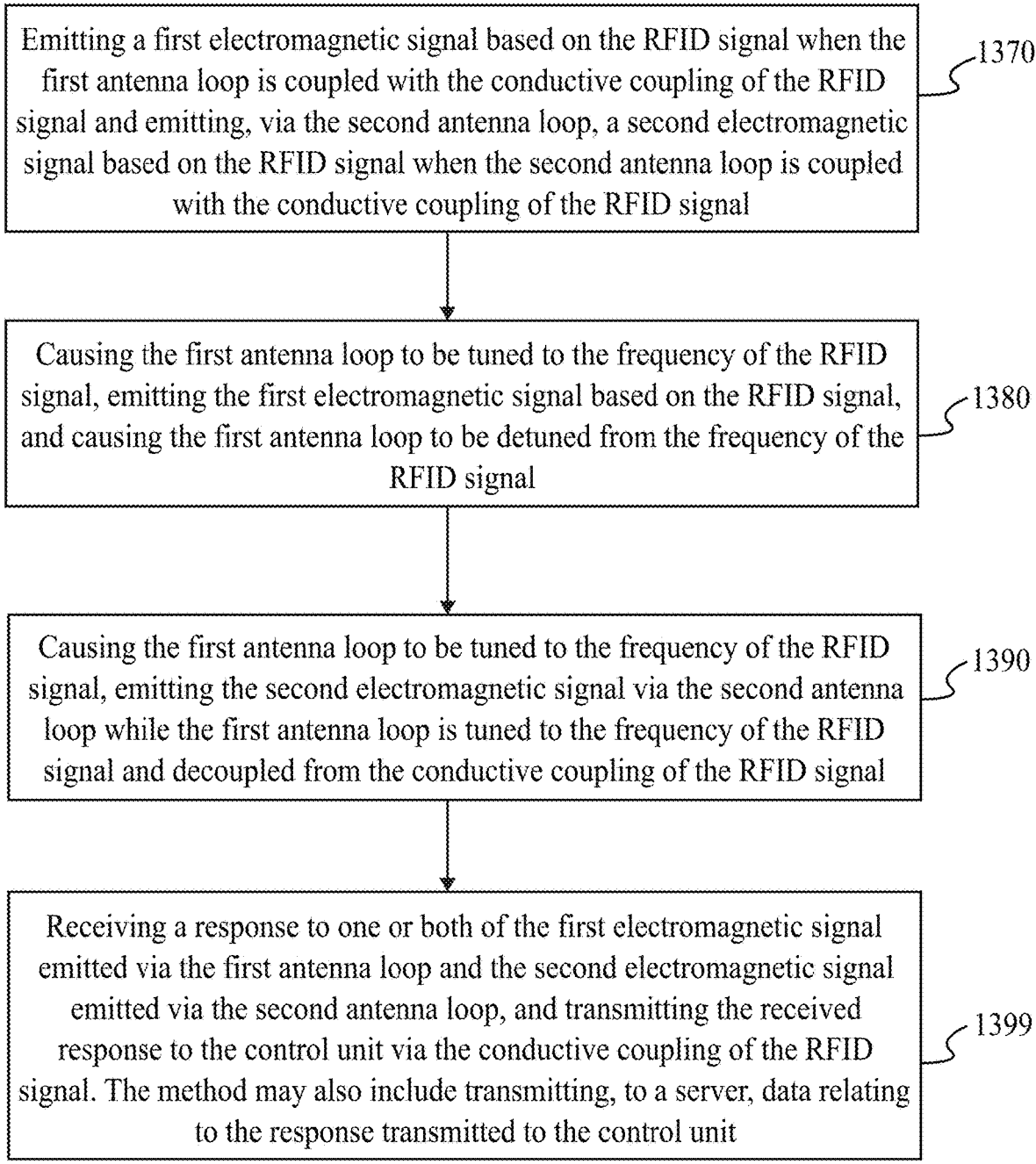

FIG. 15B further illustrates the example method for managing inventory in accordance with aspects of the present disclosure and in conjunction with FIG. 15A. The method may also include emitting, via the first antenna loop, a first electromagnetic signal based on the RFID signal when the first antenna loop is coupled with the conductive coupling of the RFID signal and emitting, via the second antenna loop, a second electromagnetic signal based on the RFID signal when the second antenna loop is coupled with the conductive coupling of the RFID signal 1370. The method may further include causing the first antenna loop to be tuned to the frequency of the RFID signal, emitting the first electromagnetic signal based on the RFID signal, and causing the first antenna loop to be detuned from the frequency of the RFID signal 1380. The method may also include, based on the control signal received at the shelf-located controller, causing the first antenna loop to be tuned to the frequency of the RFID signal, emitting the second electromagnetic signal via the second antenna loop while the first antenna loop is tuned to the frequency of the RFID signal and decoupled from the conductive coupling of the RFID signal 1390. The method may also include receiving, from an RFID device associated with at least one item stored by the at least one shelf, a response to one or both of the first electromagnetic signal emitted via the first antenna loop and the second electromagnetic signal emitted via the second antenna loop, and transmitting the received response to the control unit via the conductive coupling of the RFID signal. The method may also include transmitting, to a server, data relating to the response transmitted to the control unit 1399.

Figure 16:
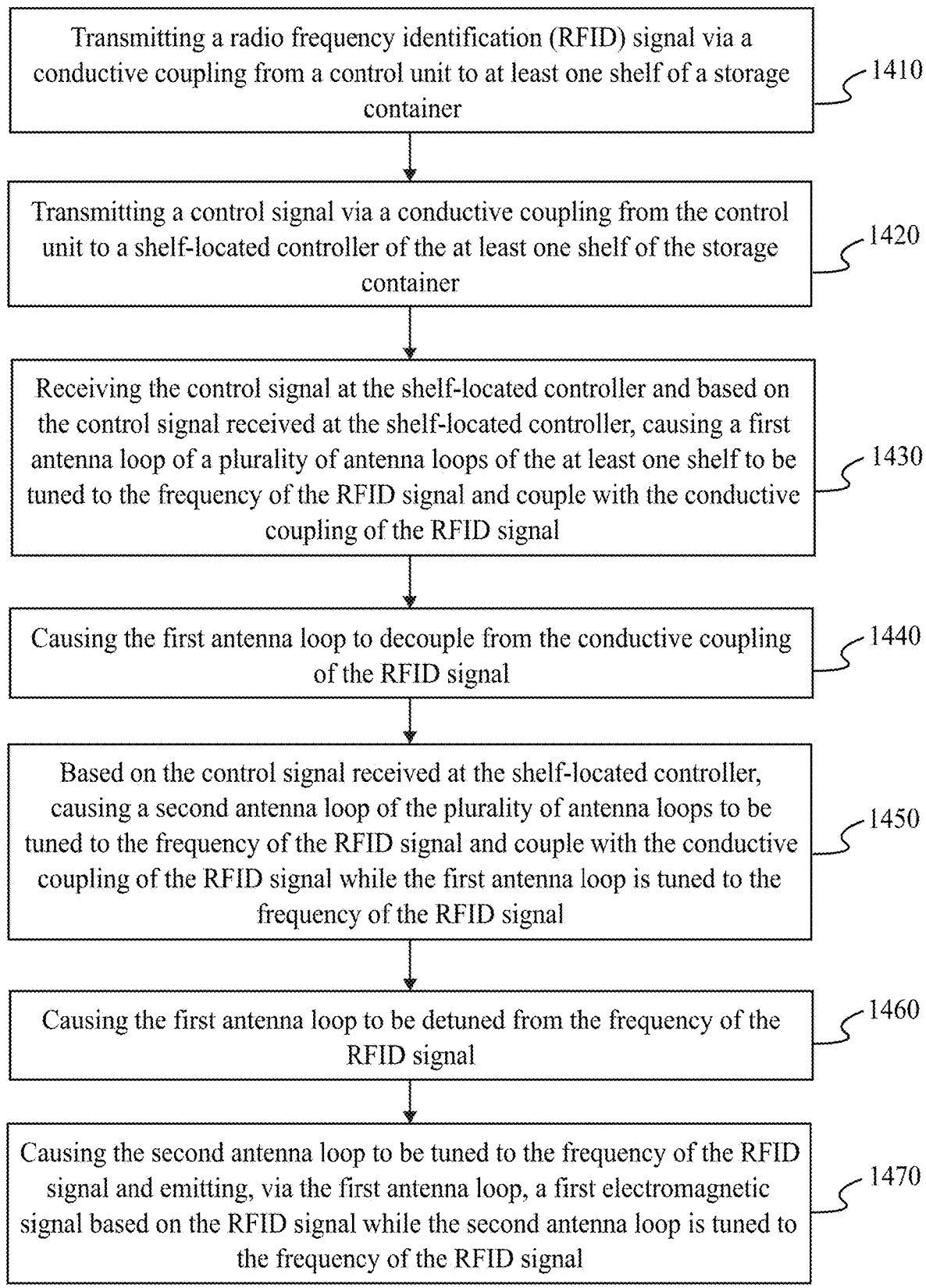
FIG. 16 illustrates another example flowchart for managing inventory in accordance with aspects of the present disclosure.

FIG. 16 illustrates another example method in accordance with aspects of the present disclosure. The method includes: (i) transmitting a radio frequency identification (RFID) signal via a conductive coupling from a control unit to at least one shelf of a storage container 1410; (ii) transmitting a control signal via a conductive coupling from the control unit to a shelf-located controller of the at least one shelf of the storage container 1420; (iii) receiving the control signal at the shelf-located controller and, based on the control signal received at the shelf-located controller, causing a first antenna loop of a plurality of antenna loops of the at least one shelf to be tuned to the frequency of the RFID signal and coupled with the conductive coupling of the RFID signal 1430; (iv) causing the first antenna loop to decouple from the conductive coupling of the RFID signal 1440; (v) based on the control signal received at the shelf-located controller, causing a second antenna loop of the plurality of antenna loops to be tuned to the frequency of the RFID signal and coupled with the conductive coupling of the RFID signal while the first antenna loop is tuned to the frequency of the RFID signal 1450; and (vi) causing the first antenna loop to be detuned from the frequency of the RFID signal 1460. The method may further include causing the second antenna loop to be tuned to the frequency of the RFID signal and emitting, via the first antenna loop, a first electromagnetic signal based on the RFID signal while the second antenna loop is tuned to the frequency of the RFID signal.

Figure 17:
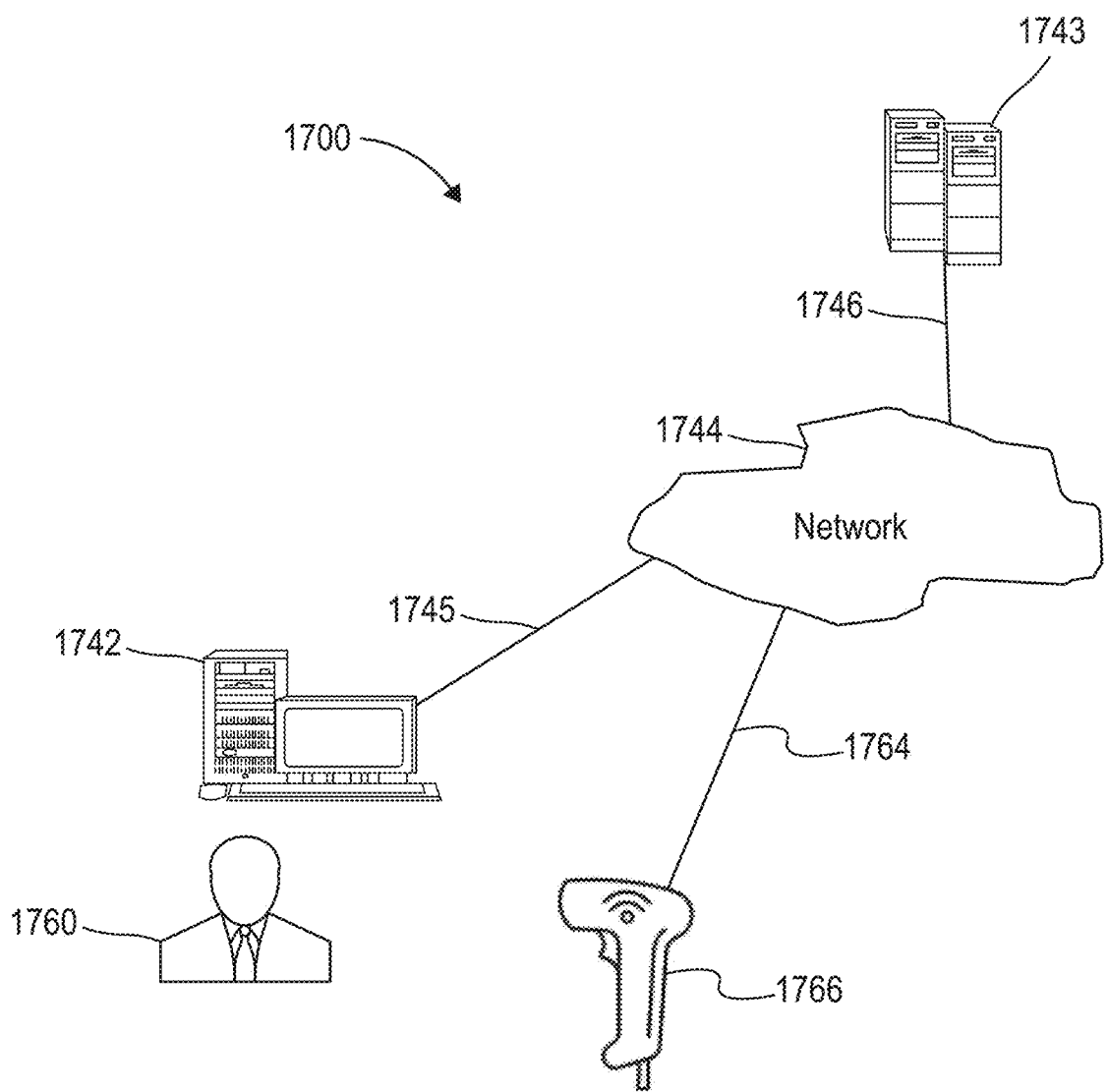
FIG. 17 illustrates a block diagram of various example system components for use in accordance with aspects of the present disclosure.

FIG. 17 is a block diagram of various example system components in accordance with aspects of the present disclosure. FIG. 17 shows a communication system 1700 including one or more accessors 1760 (also referred to interchangeably herein as one or more "users"), one or more terminals 1742 and one or more peripheral input devices 1766. Terminal 1742 and peripheral input device 1766 may include, for example, elements of systems 1110, 1120 and 1130, shown and described in conjunction with FIG. 13. In one aspect, data for use in accordance with aspects described herein may be input and/or accessed by accessors 1760 via terminal 1742, or peripheral input device 1766, such as personal computers (PCs), minicomputers, mainframe computers, microcomputers, telephonic devices, or wired/wireless devices, such as personal digital assistants ("PDAs") and RFID readers (e.g., handheld, mobile, cabinets, etc.) coupled to a server 1743, such as a PC, minicomputer, mainframe computer, microcomputer, or other device having a processor and a repository for data and/or connection to a repository for data, via, a network 1744 for instance, such as the Internet or an intranet, and couplings 1745, 1746, 1764. The terminal 1742 and/or peripheral input device 1766 may be used to read, add or scan the RFID tag to the systems, described above. Further, the terminal 1742 peripheral input device 1766 may be implemented to monitor, remove, add, scan, etc. the RFID tags of the system described above. The couplings 1745, 1746, 1764 may include wired, wireless, or fiberoptic links. In another example variation, the method and system in accordance with aspects described herein operate in a stand-alone environment, such as on a single terminal.

The aspects discussed herein can also be described and implemented in the context of computer-readable storage medium storing computer-executable instructions. Computer-readable storage media includes computer storage media and communication media, and may be, flash memory drives, digital versatile discs (DVDs), compact discs (CDs), floppy disks, and tape cassettes. Computer-readable storage media can include volatile and nonvolatile, removable and non-removable media implemented in any method or technology for storage of information such as computer readable instructions, data structures, modules or other data.

While the aspects described herein have been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects, as set forth above, are intended to be illustrative, not limiting. Various changes may be made without departing from the spirit and scope of the disclosure. Therefore, the disclosure is intended to embrace all known or later-developed alternatives, modifications, variations, improvements, and/or substantial equivalents.

Thus, the claims are not intended to be limited to the aspects shown herein, but are to be accorded the full scope consistent with the language of the claims, wherein reference to an element in the singular is not intended to mean "one and only one" unless specifically so stated, but rather "one or more." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

It is understood that the specific order or hierarchy of the processes/flowcharts disclosed is an illustration of example approaches. Based upon design preferences, it is understood that the specific order or hierarchy in the processes/flowcharts may be rearranged. Further, some features/steps may be combined or omitted. The accompanying method claims present elements of the various features/steps in a sample order, and are not meant to be limited to the specific order or hierarchy presented.

Further, the word "example" is used herein to mean "serving as an example, instance, or illustration." Any aspect described herein as "example" is not necessarily to be construed as preferred or advantageous over other aspects. Unless specifically stated otherwise, the term "some" refers to one or more. Combinations such as "at least one of A, B, or C," "at least one of A, B, and C," and "A, B, C, or any combination thereof" include any combination of A, B, and/or C, and may include multiples of A, multiples of B, or multiples of C. Specifically, combinations such as "at least one of A, B, or C," "at least one of A, B, and C," and "A, B, C, or any combination thereof" may be A only, B only, C only, A and B, A and C, B and C, or A and B and C, where any such combinations may contain one or more member or members of A, B, or C. Nothing disclosed herein is intended to be dedicated to the public regardless of whether such disclosure is explicitly recited in the claims.

What is claimed is:

1. A system, comprising:
    a radio frequency identification (RFID) storage container comprising a control unit, a first shelf having a first plurality of antenna loops comprising a first array of antennas and a second shelf having a second plurality of antenna loops comprising a second array of antennas, the RFID storage container configured to:
    transmit, via the control unit, a first RFID emission signal via a first transmission wire to the first shelf of the RFID storage container and a second RFID emission signal via a second transmission wire to the second shelf of the RFID storage container;
    emit, via a first antenna loop of the first array of antennas, a first electromagnetic signal based on the first RFID emission signal;
    emit, via a second antenna loop of the first array of antennas, a second electromagnetic signal based on the first RFID emission signal;
    receive, from one or more RFID tags associated with one or more corresponding products stored by the RFID storage container, a first responsive signal from the one or more RFID tags upon activation of the one or more RFID tags by one or more of the first and second electromagnetic signals;
    emit, via a first antenna loop of the second array of antennas, a third electromagnetic signal based on the second RFID emission signal;
    emit, via a second antenna loop of the second array of antennas, a fourth electromagnetic signal based on the second RFID emission signal;
    receive, from one or more of the RFID tags, a second responsive signal from the one or more RFID tags upon activation of the one or more RFID tags by one or more of the third and fourth electromagnetic signals; and
    transmit a status of the one or more products based on the reception of the first response signal and the second responsive signal from the one or more RFID tags;
    a remote computing device configured to:
    receive the status of the one or more products; and
    monitor an inventory based on the status of the one or more products.

2. The system of claim 1, wherein the first shelf is in communication with and coupled to a shelf controller configured to communicate with the control unit and selectively couple one or more antenna loops of the first array of antennas with the first transmission wire.

3. The system of claim 1, wherein the first transmission wire and the second transmission wire are equal in length.

4. The system of claim 2, wherein the first shelf is configured to activate one or more RFID tags applied to products stored on either or both of the first shelf and the second shelf.

5. The system of claim 4, wherein the RFID storage container is configured to receive the first responsive signal from a designated one of the RFID tags upon activation of the designated RFID tag by one or more of the first and second electromagnetic signals, and to receive the second responsive signal from the designated RFID tag upon activation of the designated RFID tag by one or more of the third and fourth electromagnetic signals.

6. The system of claim 2, wherein the first array of antennas includes a plurality of antenna loops, wherein each antenna loop of the first array of antennas is communicatively coupled to a switching circuit.

7. The system of claim 6, wherein a portion of each antenna loop of the first array of antennas overlaps with at least one other antenna loop of the first array of antennas.

8. The system of claim 6, wherein the switching circuit is configured to activate a designated antenna loop of the first array of antennas, while at least one other antenna loop of the first array of antennas remains in an open circuit status.

9. The system of claim 1, wherein the control unit is configured to adjust a power level of the RFID emission signal transmitted to the first shelf to determine a location of a given product stored on the first shelf.

10. The system of claim 9, wherein the control unit is further configured to variably adjust the power level of the transmitted first RFID emission signal, and to determine a threshold readability of the one or more RFID tags located proximal to the first shelf.

11. A radio frequency identification (RFID) storage container, comprising:
    a control unit configured to transmit a first RFID emission signal and a second RFID emission signal via a first transmission wire and a second transmission wire, respectively;
    a first shelf comprising a controller and an array of antennas, the first shelf being configured to:
    receive, at the controller, the first RFID emission signal from the control unit via the first transmission wire;
    emit, via the array of antennas, an electromagnetic signal in response to receipt of the first RFID emission signal;
    receive, from one or more RFID tags associated with one or more corresponding products stored on the first shelf, a responsive signal from the one or more RFID tags upon corresponding receipt of the electromagnetic signal; and transmit to the control unit detected responses of the one or more products based on the response to the electromagnetic signal,
wherein the first transmission wire and the second transmission wire are equal in length.

12. The RFID storage container of claim 11, wherein the array of antennas includes a plurality of antennas, wherein two or more antennas of the plurality of antennas are communicatively coupled to a switching circuit.

13. The RFID storage container of claim 11, wherein the control unit is configured to adjust a power level of the first RFID signal transmitted to the first shelf to determine a location of a given product stored on the first shelf.

14. The RFID storage container of claim 13, wherein the control unit is further configured to variably adjust the power level of the transmitted first RFID emission signal, and to determine a threshold readability of RFID tags proximal to the first shelf or a second shelf.

15. A method for managing inventory, the method comprising:
    transmitting a first radio frequency identification (RFID) signal via a first transmission wire of a first conductive coupling from a control unit to a first shelf of a storage container;
    transmitting a second radio frequency identification (RFID) signal via a second transmission wire of a second conductive coupling from the control unit to a second shelf of the storage container;
    transmitting a control signal via the first conductive coupling from the control unit to a shelf-located controller of the first shelf of the storage container;
    receiving the control signal at the shelf-located controller of the first shelf;
    based on the control signal received at the shelf-located controller of the first shelf:
        causing a first antenna loop of a first plurality of antenna loops of the first shelf to couple with the first transmission wire of the first RFID signal,
        causing the first antenna loop of the first plurality of antenna loops to decouple from the first transmission wire of the first RFID signal,
        causing a second antenna loop of the first plurality of antenna loops to couple with the first transmission wire of the first RFID signal,
        causing the second antenna loop of the first plurality of antenna loops to decouple from the first transmission wire of the first RFID signal;
    receiving the control signal at the shelf-located controller of the second shelf; and
    based on the control signal received at the shelf-located controller of the second shelf:
        causing a first antenna loop of a second plurality of antenna loops to couple with the second transmission wire of the second RFID signal,
        causing the first antenna loop of the second plurality of antenna loops to decouple from the second transmission wire of the second RFID signal,
        causing a second antenna loop of the second plurality of antenna loops to couple with the second transmission wire of the second RFID signal, and
        causing the second antenna loop of the second plurality of antenna loops to decouple from the second transmission wire of the second RFID signal.

16. The method of claim 15, wherein the first transmission wire and the second transmission wire are equal in length.

17. The method of claim 15, the method further comprising:
    emitting, via the first antenna loop of the first plurality of antenna loops, a first electromagnetic signal based on the first RFID signal when the first antenna loop of the first plurality of antenna loops is coupled with the first transmission wire of the first RFID signal; and
    emitting, via the second antenna loop of the first plurality of antenna loops, a second electromagnetic signal based on the first RFID signal when the second antenna loop of the first plurality of antenna loops is coupled with the first transmission wire of the first RFID signal.

18. The method of claim 17, wherein the first RFID signal has a designated frequency range, the method further comprising causing the first antenna loop of the first plurality of antenna loops to be tuned to within the designated frequency range of the first RFID signal, emitting the first electromagnetic signal based on the first RFID signal, and causing the first antenna loop of the first plurality of antenna loops to be detuned from within the designated frequency range of the first RFID signal.

19. The method of claim 17, the method further comprising, based on the control signal received at the shelf-located controller of the first shelf, causing the first antenna loop of the first plurality of antenna loops to be tuned to a designated frequency range of the first RFID signal, emitting the second electromagnetic signal via the second antenna loop of the first plurality of antenna loops while the first antenna loop of the first plurality of antenna loops is tuned to within the designated frequency range of the first RFID signal and decoupled from the first transmission wire of the first RFID signal.

20. The method of claim 17, the method further comprising:
    receiving, from an RFID device associated with at least one item stored by the first shelf, a response to one or both of the first electromagnetic signal emitted via the first antenna loop of the first plurality of antenna loops and the second electromagnetic signal emitted via the second antenna loop of the first plurality of antenna loops; and
    transmitting the received response to the control unit via the first conductive coupling of the first RFID signal.

\* \* \* \* \*